(12) United States Patent
Jackson et al.

(10) Patent No.: US 6,461,644 B1
(45) Date of Patent: *Oct. 8, 2002

(54) ANESTHETIZING PLASTICS, DRUG DELIVERY PLASTICS, AND RELATED MEDICAL PRODUCTS, SYSTEMS AND METHODS

(75) Inventors: Richard R. Jackson, One Atlantic Ave., Swampscott, MA (US) 01907; John N. Williams, Boston, MA (US)

(73) Assignee: Richard R. Jackson, Swampscott, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/070,940

(22) Filed: Apr. 30, 1998

Related U.S. Application Data

(63) Continuation-in-part of application No. PCT/US97/04948, filed on Mar. 27, 1997, and a continuation-in-part of application No. 08/622,190, filed on Mar. 25, 1996, now Pat. No. 5,810,786.

(60) Provisional application No. 60/040,481, filed on Mar. 7, 1997.

(51) Int. Cl.[7] ................................. A61K 9/70

(52) U.S. Cl. .................. 424/499; 514/277; 514/408; 514/529; 514/532; 514/534

(58) Field of Search ................. 424/449; 514/277, 514/408, 529, 532, 534

(56) References Cited

U.S. PATENT DOCUMENTS 5,810,786 A * 9/1998 Jackson et al. ............. 604/265

* cited by examiner

*Primary Examiner*—Michael A. Williamson
(74) *Attorney, Agent, or Firm*—Fish & Richardson P.C.

(57) ABSTRACT

Anesthetizing plastic or other drug delivery polymer system including a hydrophobic polymer and a drug that has an aromatic ring.

32 Claims, 6 Drawing Sheets

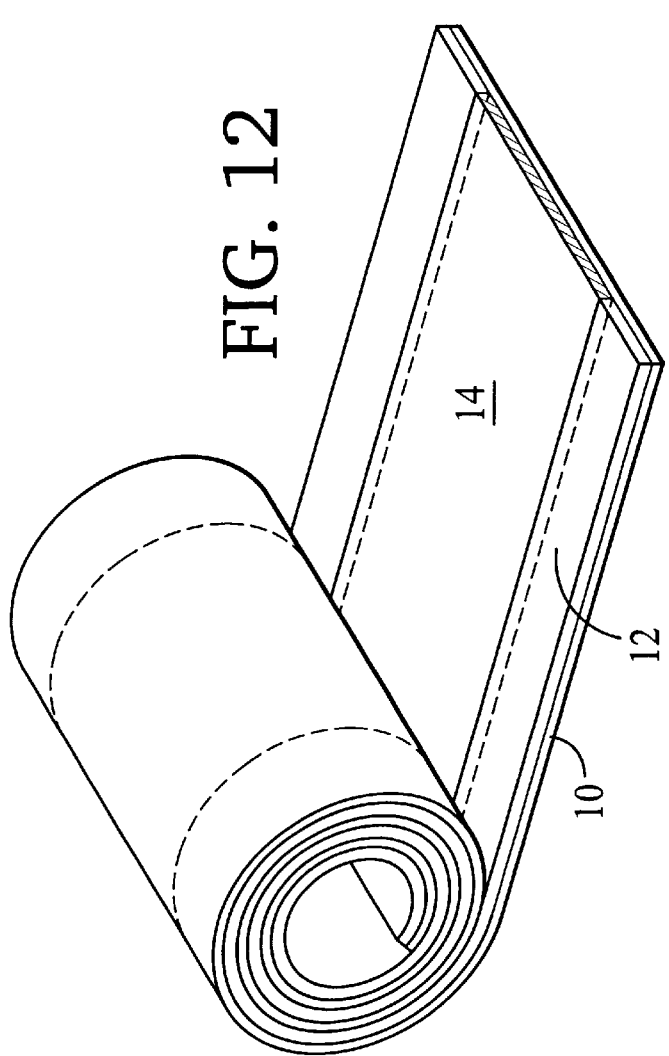
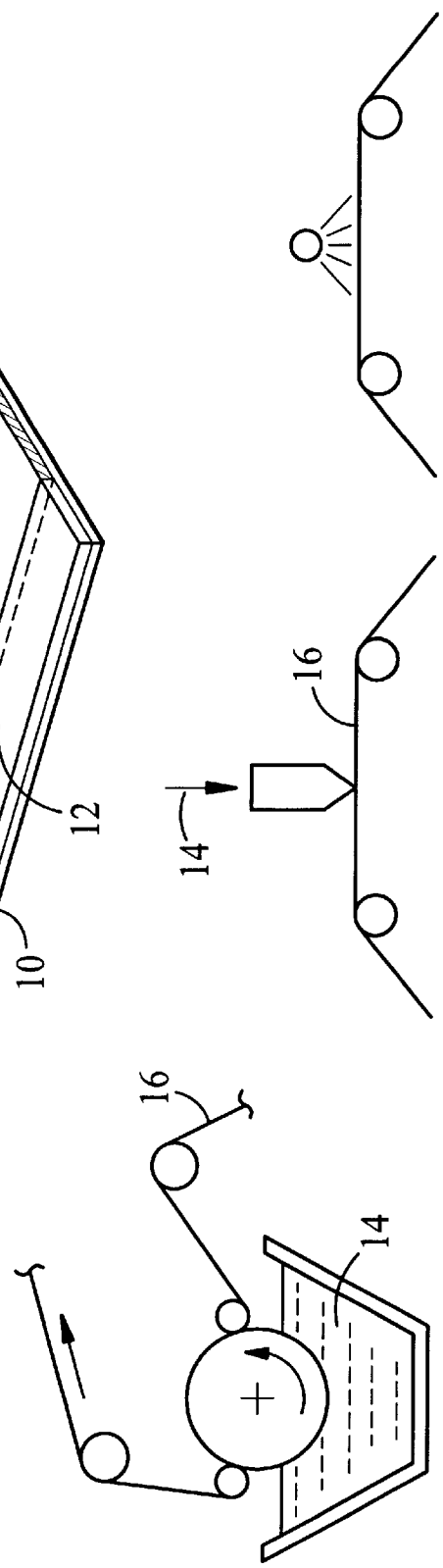

ANESTHETIZING PLASTICS, DRUG DELIVERY PLASTICS, AND RELATED MEDICAL PRODUCTS, SYSTEMS AND METHODS

This application is a continuation-in-part of; PCT U.S. Ser. No. 97/04948, filed Mar. 27, 1997, U.S. Ser. No. 08/622,190, filed Mar. 25, 1996 now U.S. Pat. No. 5,810,786, and Provisional Application, Ser. No. 60/040,481, entitled Anesthetizing Plastics, Drug Delivery Plastics and Related Medical Products, Systems and Methods filed by the inventors on Mar. 7, 1997. Related disclosure will be found in PCT/US 94/00492 published as WO95/08305 on Mar. 30, 1995, U.S. Ser. 126,970 filed Sep. 24, 1993, now U.S. Pat. No. 5,417,671, issued May 23, 1995 and U.S. Ser. No. 527,593, filed May 23, 1990, now U.S. Pat. No. 5,279,594, issued Jan. 18, 1994, each of which is hereby incorporated by reference as if fully set forth, and from each of which the present application, for U.S. purposes, is a continuation-in-part.

According to one aspect of this invention, it has been discovered that anesthetics of amide or ester type, such aslidocaine base, tetracaine base, propafenone or other drugs of similar structure, are highly soluble, or otherwise can be incorporated in large, effective concentrations, in conventional polymers. Under suitable conditions, the drug is found to migrate gradually and steadily to the surface of the plastic. Because of the large concentration found possible, in many cases the percentage reduction of drug present relative to the initial amount of drug, decreases only gradually with time, and provides zero order time dependence in rate over prolonged periods of use. Unique ways have been realized for employing this phenomenon. The plastic is employed as a long-term protective reservoir for the drug. In many advantageous cases, the plastic forms the exterior portion of a functional wall or component of a device as well as serving as a drug reservoir. In other cases fine particles of the plastic are employed as the reservoir. In important cases the drug is of base form and/or is more soluble in the plastic than in water. In important cases, the plastic is a hydrophobic film-forming or structural resin.

In certain instances, the plastic reservoir material itself is directly exposed to body tissue as in the case of contact with the mucosal tissue or the skin. In certain instances, one or more intervening layers are included to determine release rate to the body or to facilitate transfer of the drug to the body or to isolate the reservoir plastic from contact with body tissue. In certain cases, as in certain dermal applications, the main limit on the dosage rate is the transmissivity of the skin itself and the reservoir serves to maintain a high or selected concentration of the drug in contact with the skin surface. In other instances, the migration rate of the drug in the resin controls the release of the drug into the patient.

The phenomenon that large concentrations of the drug can be incorporated in conventional plastic resin is found to be especially applicable to FDA-approved structural and film-forming thermoplastics such as fully polymerized polyvinyl chloride (PVC). By the techniques disclosed here and in the preceding patents and patent applications referenced above, PVC in which the drug is incorporated is employed as drug-carrying granules or to coat, print or to form the structure of tubes, films, sheets, bandages, coverings, rods, foams, molded devices, sutures, other medical devices, ingestible formulations, etc.

In a wide variety of important cases the drugs in base form, when used in significant quantities, are found to demonstrate a surprising plasticizing action upon compatible plastic polymers. This facilitates the making of safe, stable and convenient products. The polymer and the drug, alone, without additional plasticizers, forms useful articles in many instances. By selection of the relative proportions of the plasticizing drug and an added therapeutically and biologically inert second plasticizer, the concentration of the drug can be selected, e.g., for selection of dosage rate, while maintaining the desired physical properties of the plastic article, such as flexibility and conformability, as in a skin patch or covering.

An anesthetizing or drug delivering effect lasting days, weeks, perhaps even months and years can be achieved by controlling the thickness of the reservoir layer, the concentration of drug present in the layer, and other parameters that govern the particular application.

The products can increase the comfort and ease of drug administration with both prescription and over-the-counter products, and in the case of anesthetic drugs, can reduce the pain of adults and children in many circumstances, reduce hospital stay, increase the use of doctor's office and outpatient care, and increase the efficiency with which medical procedures may be accomplished.

According to one aspect of the invention, it has been discovered that effective concentrations of topical anesthetic compound at contacted tissue, suitable for maintaining topical anesthesia (concentrations that are, generally, extremely large compared to other classes of drugs) can be self-administered by a wall of a medical device by selection of particular materials and particular topical anesthetics that cooperatively meet certain selection criteria. The wall material and the topical anesthetic are selected such that (1) the necessary amount of topical anesthetic "dissolves", i.e. forms a true solution in the wall material, while (2) the topical anesthetic is more soluble in the polymer than in water and (3) the concentration of the topical anesthetic compound in the wall material is such that when the wall is in contact with a body passage, the compound diffuses to a surface of the body at a rate effective in maintaining anesthesia.

The first and third criteria assure that the needed large amount of topical anesthetic can be incorporated and uniformly administered wherever tissue contacts occurs, while the first and second criteria help to enable criteria 3 to be met by assuring that the topical anesthetic, while effective, neither causes adverse systemic reaction of the patient by too rapid release, nor is wasted too soon from the surface of the device if in contact with aqueous body fluid. These three cooperating criteria enable a sufficient concentration of the topical anesthetic to be maintained at the tissue to maintain topical anesthesia for an extended time. Thus, the patient's long term discomfort is successfully eased.

The presently most preferred wall polymer for this aspect of the invention is polyvinyl chloride, while another preferred wall material is vinyl urethane copolymer. Presently preferred topical anesthetics for this aspect of the invention are lidocaine base, 50—50 mixtures of lidocaine and prilocaine and tatracaine. Dibucaine base also meets the criteria.

Applicant's Example 1 in U.S. Pat. No. 5,279,594 dramatically demonstrates the principle. In this case polyvinyl chloride wall-forming polymer and lidocaine base anesthetic are employed. True solution of an effective quantity is achieved by exposing the wall polymer to an atmosphere containing the topical anesthetic sublimed in a vacuum chamber at elevated temperature. Note that lidocaine base is insoluble in water and thus is more soluble in the polymer than in water. This is to be distinguished from the commonly used hydrochloride or salt of this compound which is highly water soluble. The dissolved amount of 550 mg of Example 1 represents a concentration in the polymer wall of 6% (based on the weight, 8 gm, of a #16 urethral catheter); the wall was shown to maintain the anesthesia effect on the tissue. The specification expressly discloses concentrations in the polymer wall that work out to 5% (Example 3) and 10% (Example 4) that are successful in achieving the prolonged level at tissue within the body needed to maintain anesthesia on.

Unlike prior attempts, applicant's solution to the serious discomfort problem is highly practical. The preferred combinations of topical anesthetic and wall polymer that meet the criteria are all medically acceptable materials. Further, it is found that the common sterilization technique of ethylene oxide can be used with these combinations.

In short, the tubes of the invention have a predictable capability to deliver prolonged, effective concentrations of topical anesthetic to the tissue wherever required along the tube length to maintain anesthesia.

Among the aspects shown in the related U.S. Pat. No. 5,279,594 are tubes that have topical anesthetic incorporated in the material of which the wall of the tube is composed, the anesthetic being more soluble in the wall material than in water.

Among the preferred features shown are the following. The base form of the anesthetic is employed. The entire wall thickness of a tube is formed of the anesthetic-polymer material. Materials are employed that enable ethylene oxide sterilizability. PVC and vinyl-urethane copolymer wall materials are employed.

In this first patent disclosure, the placement of an anesthetizing urethral catheter in a patient for eight hours of pain relief is also described. Also, surgery performed with topically anesthetizing endotracheal tubes in dogs is described in which it is shown to be possible to use lower concentrations of general anesthetic because of the local anesthetizing effect of the endotracheal tube.

Use of lidocaine, an acetamide, and dibucaine, an amide are shown. Specific topically anesthetizing products described are a urethral tube, an endotracheal tube, a nasogastric tube and elastic film of anesthetizing plastic.

A number of methods for making these products are shown in this first patent, including employing a process solution to apply the anesthetic as a film to a preformed structure, from which the process solvent is subsequently evaporated; heating and pressing to cause the anesthetic to enter into solution in the plastic while forming a sheet or film; and employing gas diffusion transfer of the drug into the plastic resin.

The disclosure of the second U.S. Pat. No. 5,417,571, discloses further features including the following.

Flexible devices are described in which high concentrations of the anesthetic in base form in the plastic substances perform the function of a plasticizer for the plastic objects.

Further topically anesthetizing medical devices are shown, including nasal tubes, Foley (balloon) catheters, feeding tubes, tubes that pass through the abdominal wall and the peritoneal cavity, and drainage tubes.

Anesthetizing films, cuffs, and balloons are shown as well as loose fitting sleeves that surround medical devices inserted in the body.

The use of a barrier layer that confines the direction of diffusion of the drug from the plastic reservoir is illustrated. Conversion of a surface layer of the anesthetic in the resin to water-soluble salt form is also described.

Products produced by extrusion and coextrusion techniques are described, as are concentrations of the anesthetic that vary across the thickness of a layer or wall, metering layers lying over the anesthetizing plastic, and use of porsigens in the plastic. Also, incorporation of the plastic in implants and use of the drug such as lidocaine for antiarrythmia medication are described.

The disclosure of the related World Pat. application, published as W095/08305 discloses further use of lidocaine and the like for antiarrythmia and antiseizure treatment. For these uses an orally ingestible form of solid particles of the drug-polymer combination is disclosed with the intention that the particles pass through the gastrointestinal tract where they release the drug and are eventually excreted.

As now explained herein, propafenone is found to enter solution or otherwise be incorporated in plastic in form enabling it to be orally administrable, or administrable by skin patch, for controlled release for antiarrythmia medication.

Principles of the invention have general applicability to drugs having at least one aromatic ring (substituted or unsubstituted benzene ring) that includes at least one free amide or amine hydrogen in its structure. In particular, drugs having at least one aromatic ring (e.g., at least one substituted or unsubstituted benzene ring), and melting point in the range of the processing temperature of thermoplastic or other heat processable resins, with the drug in base form (e.g., includes at least one free amide or amine hydrogen in its structure), can be dissolved or otherwise incorporated in effective concentrations in heat processable resin, typically at elevated temperature. In many instances, the concentrations of the drug can be very high, e.g. in excess of 10% by weight, in many cases preferably in excess of 20% by weight, and most preferably in excess of 30% or 40% by weight. For many conventional low or medium molecular weight resins having processing temperatures between about 250° F. and 350° F., numerous of the drugs have been found to be soluble or otherwise capable of incorporation at useful levels. For high molecular weight resins, with processing temperatures up to about 450° F., additional drugs may be dissolved or incorporated at useful levels.

In the cooled form, the solution of resin and drug may behave as they do in conventional plasticized PVC, forming, in essence, a solid gel, which, in many useful cases, has a desirable rubbery consistency. In other cases, a network of the drug is distributed through the cooled reservoir resin, in molecular, crystalline or amorphous form, that can be utilized via migration through the resin or by access pathways provided in the reservoir.

In other cases, rather than employ heat processing other techniques, including use of solvents and vapor transfer, are used to incorporate the drug in compatible resins.

In a preferred form, drugs employed according to the invention have the form:

where:
  Bz is a substituted or unsubstituted benzene ring;
  Z is an ester or amide linkage;
  and each $R^1$ and $R^2$, individually, is Hydrogen or an alkyl group, or together form a 5 or a 6 member ring with the Nitrogen, and n is an integer.

For a desired drug, the resin system is selected to be compatible with the drug such that, at processing conditions and conditions of use, no adverse effects or reactions occur that deprive the drug of its efficacy, or the degree of mobility of the drug desired. For instance, when using thermal processing techniques, the ingredients are selected to withstand the temperatures of processing and the shear forces that are involved in the mixing, milling, or extruding that is involved and to be biocompatible when exposed to the patient.

It has been observed, specifically, according to the invention, that numerous drugs are highly soluble in polyvinyl chloride, chlorinated polyethylene and ethylene propylene, as well as in methyl methacrylate and other acrylics. It has been observed that these drugs have at least one benzene ring, are of base (e.g., free amine or amide) form. They have a lower melting point than the hydrochloric salt form of the drug, that makes them practically processable with thermoplastic resins, e.g. at temperatures in the range of about 250° F. to 350° F., and up to 450° F. for high molecular weight resins.

As has been previously indicated above, it has been observed that the drugs can have a plasticizing effect on resin.

Broadly speaking, the invention is indicated to be applicable to resins or polymers in which plasticizers can be incorporated or in which phthalates, glycolates or citrate esters are soluble, or in which plasticizers or other additives with at least one aromatic ring can be incorporated.

More specifically, it has been realized that the solubility or ability to be incorporated in resins of such drugs of such molecular structure as described, in a general way, is predictable from the behavior in resins of comparable plasticizers such as phthalate, glycolate, and citrate esters which are also characterized by an aromatic ring. For the class of drugs having an aromatic ring, and especially a single aromatic ring, it can be reasonably stated that such drugs will have solubilities or the ability to be incorporated in the range of plastics in which plasticizers of similar molecular structure are soluble or can be incorporated. Phthalate esters are soluble, or can be incorporated e.g. in polymers and copolymers of polyvinylchloride, chlorinated polyethylene, cellulose nitrate, ethyl cellulose, cellulose acetate, polystyrene, polyvinyl butyryl, acrylic resins, alkyl alkylacrylates, acrylonitrile rubbers, and chlorinated rubbers such as neoprene. Drugs having a single benzene ring and structure similar to the plasticizers are likewise soluble or incorporatable in the range of resins, as a step in the preparation of a drug delivery composition.

Accordingly, further aspects of the invention include the following features. The drug has a single benzene ring; the drug of base form is soluble in resins or polymers in which phthalate, glycolate, or citrate esters are soluble; the drug has local anesthetic properties (whether or not it is generally used as a local anesthetic); the drug is an antiarrhythmic or antiseizure drug having local anesthetic properties; the antiarrhythmic drug is propafenone or lidocaine; the drug is a local or topical anesthetic medication; the drug is an adrenergic blocking drug such as atenol; the drug is a sympathomimetic drug such as pseudoephedrine, terbutaline or phenylpropanolamine; the drug is an analgesic or antipyretic such as acetaminophen, phenacetin or ibuprofen; the drug is a stimulant of the nervous system, e.g. a psychostimulant such as methylphenidate.

Structurally related drugs may be incorporated in a number of biocompatible polymers or copolymers without preventing the drug from having efficacy. Examples include resins selected from polyvinyl chloride, other polymerized vinyl halides, chlorinated polyethylene, other halogenated polyolefins, cellulosic resins such as cellulose nitrate, ethyl cellulose, cellulose acetate, polystyrene, polyvinyl butyral, alkyl alkylacrylate resins (e.g., methyl methacrylate, ethyl methacrylate), or alkyl acrylates, acrylonitrile rubbers, and halogenated rubbers (e.g., chlorinated neoprene), polyesters such as polyethylene terepthalate, polyamides such as nylon and polyformaldehyde.

Also of consequence is the realization that drugs which have an observable anesthetic characteristic (even if the main use of the drug is not for anesthesia, but for other purposes such as antiarrhythmia or other treatment of the neurophysiological system of the body) can be administered in prolonged manner by resin systems including thermoplastic resin, in which the base form of the drug has been dissolved or is otherwise incorporated.

In certain resins, certain drugs are found to be so highly soluble that the use of relatively low molecular weight resins is possible. For instance polyvinyl chloride with specific viscosity of about 225 (intrinsic viscosity of between about 96 and 99) has been demonstrated to receive in solution as much as 50% of the drugs lidocaine and the eutoclic 50% lidocaine and 50% prilocaine. Such resins are preferred when forming tube, sheet-like or fiber material in which considerable flexibility of the tube, sheet or fiber is desired.

For other applications, such as orally administratable granules of fine or coarse powders, it is desired to form an extrusion of the resin with dissolved drug, and then to grind it to form the granules. For this purpose a relatively high molecular weight, rigid resin may be preferred for ease of grinding. The high molecular weight, long molecules of such resins permit the attainment of higher processing temperatures and longer residence times in the mill or other processing equipment that is employed to dissolve or distribute the drug into the resin. This leads to increase in the amount of the drug that can be incorporated. In turn, this leads to a wider practical range of choice of the resin, permitting use of resins which have other desirable properties, such as meeting requirements of regulatory agencies and the like for prolonged use within the body, as well as to attain desirable process, storage, performance, and economic characteristics.

For those therapies in which more than one drug that is soluble in resin can be selected, another criteria for choice of the system to be employed is the fugitive or diffusive character of the drug within the particular resin. This may be estimated based upon the molecular structure of the drug, the shorter and less complicated the molecule, the more fugitive. For any particular desired therapy, demonstrations with selected drugs and resins are readily conducted to enable empirical observation. Final choice of the constituents and relationships based upon observed, reproducible results is a matter for those of ordinary skill in formulating drug and resin compositions.

As has been indicated, the discoveries described above, which arose in respect of topical anesthetics, have led to the realization that systems of the invention have generality beyond drugs that are known to have anesthetic characteristics. Thus, from the similarity of chemical structure and known characteristics of drugs, plasticizers and resins, it is realized that a wide range of drugs having sufficient unsaturated moieties, aromatic or heteroaromatic moieties, or similar structure can be delivered employing the present invention. Among these drugs are atenol, pseudoephedrine, terbutaline, phenylpropanolamine, acetaminophen, ibuprofen, phenacetin and methylphenidate.

Thus the present invention teaches and achieves new modes of drug delivery. It enables administration of drugs thought previously to have insufficient half life when administered systemically for particular therapies, and enables delivery, in prolonged fashion, of drugs that heretofore have been required to be administered at disadvantageous frequency or by disadvantageous modes.

In another aspect, the present invention teaches the applicability, in a new way, of general knowledge of the plastics industry as to compatibility of particular plasticizers, solvents, and other additives with known structural and film forming plastic systems. The molecular structure of the base form of a drug having a benzene ring, that is desired to be delivered, is compared with the molecular structure and concentrations used of proven plasticizers, solvents or additives for plastics systems. On the criteria of the similarities, a small group of candidate resins is identified. Simple mixing and heating of a substantial concentration of the drug with the resin, as between two plates under pressure, enables identification of the better combinations for compatibility of the introduced materials and enables observation of the efficacy of the system. In the case of topical anesthetic products, efficacy is readily observed based on the onset time for numbness, and the degree of numbness achieved. In other cases, migration of the drug from the novel reservoir through cadaver tissue can be observed.

To further expand upon the applicability of prior knowledge, in respect for instance of polyvinyl halide products, one should consult the literature beginning with U.S. Pat. Nos. 1,929,453, 1,983,949 and 2,188,396 to Waldo Semon, the discoverer of soluble plasticizers for polyvinyl halide products. The disclosure of those patents is hereby incorporated by reference. These references and the many references that followed, that have advanced the understanding, further indicate the plasticizer or solvent compositions with which drugs for a vinyl system can be compared. Consulting the literature readily provides similar references for other candidate resin systems in light of the present teachings.

The drug compositions according to the inventions are formulated to advantage in various ways. Resin granules are prepared such as fine or coarse powder in tablet or capsule form suitable for oral administration. The resin in orally administratable form has characteristics whereby the drug is released in the stomach and/or in the lower portion of the gastrointestinal system after which the resin is eliminated through the bowel. A protective coating on the particles may be employed to protect the composition from the acidic portions of the gastric tract.

The resin may be selected out of safety and regulatory considerations to reside as an implant or covering for prolonged periods in contact with tissue or body fluid; thus the resin may be formed as a thin, flexible wall or fiber strip or rod exposed to contact tissue; the resin is configured to perform an added function, e.g. to perform the added function of a fluid-contacting tube, feeding tube, drainage tube, or an irrigation or fluid drug administration tube or the covering of an endoscope or other examination device.

In some cases, the resin is loaded with (has dissolved or otherwise incorporated in it) a plurality of drugs, wherein the plurality includes drugs that have the same or different properties.

The resin also is advantageously configured to deliver local or topical anesthetic in the exterior region of an incision or wound, e.g. the resin is configured to form a functional bandage or compress, or a transdermal patch for intact skin.

Another aspect of the invention is a wound or incision-contacting device formed to reside beneath the closure of a surgical point, and formed at least in part of thermoplastic resin in which a topical anesthetic or other drug is dissolved or otherwise incorporated according to the invention. Such a device can reduce local pain and discomfort and promote healing.

Certain preferred embodiments of the wound or incision-contacting devices have one or more of the following features.

The device includes a drug in base form dissolved in resin and in water soluble salt form associated with the resin. The salt form is a hydrochloride salt. The device includes hydrophobic resin in which the base form is dissolved and in which the salt form is imbibed in aqueous solution in porsigens or other receptive portions or is in the form of crystal deposits that result from imbibing and subsequent drying. The device is a tube having a surface that contacts tissue to be treated. The device is a film having a surface that contacts tissue to be treated. The device is present in a compress or bandage. The device is formed at least in part of thermoplastic fibers in which the drug is present. The device is a suture formed at least in part of thermoplastic resin in which the drug is dissolved or otherwise incorporated. The fibers are at least part of a textile material. The material is a non-woven. The fibers are hydrophobic. The hydrophobic fibers are combined with hydrophilic fibers that contain an aqueous substance that promotes release and transport of the drug from the hydrophobic resin. The device comprises a cotton or other absorbent material upon which is applied, e.g. by printing or coating, in a pattern, a polymer in which the drug is incorporated. The device is combined with a fluid, ointment or adhesive that promotes transport of the drug. The fluid, ointment or adhesive contains a drug, and the drug from the resin is effective to replenish the drug in the fluid, ointment or adhesive. The drug in the fluid, ointment or adhesive and the drug dissolved or incorporated in the resin include topical anesthetics. The fluid, ointment or adhesive includes surfactant or other permeation enhancers that promote diffusion of the drug through tissue, such as the skin. The fluid, ointment or adhesive includes a thickener. The fluid, ointment or adhesive includes carboxypoly methylene (Carbopol™). The fluid, ointment or adhesive that cooperates with the drug dissolved or otherwise incorporated in the resin includes a combination of topical anesthetics and an emulsifier such as Tween™ (a polyoxyethylene fatty acid ester). The combined anesthetics in the fluid, ointment or adhesive are prilocaine and lidocaine.

Another aspect of the invention is a wound or incision treating device comprising fibers or constituents of hydrophobic resin in which a drug, and especially an anesthetic base, is dissolved.

Another aspect of the invention is a wound or incision treating device comprising fibers or constituents of hydrophilic resin in which a salt form of anesthetic is imbibed or deposited as crystals.

Certain preferred embodiments of these aspects have one or more of the following features. The device comprises a combination of fibers or constituents of hydrophobic and hydrophilic resin. The fibers or constituents of both types of resin carry a drug. An aqueous solution in the hydrophilic fibers is adapted to assist in transport or migration of base-form drug in the hydrophobic resin. The aqueous solution in the hydrophilic fibers is acidic and adapted to convert the base form of the drug to a water soluble salt.

Topically anesthetizing plastic fibers, sutures and textile layers, functional bandages and compresses and methods of manufacture of such devices are also provided.

Additional important features of the invention include transdermal patches employed to apply topical anesthetic or drug to or through the skin, use of high concentrations of lidocaine as a tackifier to form a tackified methyl methacrylate-based adhesive useful as a transfer layer or as a significant drug releasing reservoir, use of plastisols for fabricating products including sheets, foams, films and coatings, formation of adherent and lubricious anesthetizing coatings and formulation of creams and other liquid suspensions and adhesives that employ solid plastic particles of e.g. PVC, in which a drug such as lidocaine is present. A drug delivery or anesthetic delivery foam ear plug, foam nasal plug, foam drug or anesthetic delivery rectal, vaginal or other suppository, a dental appliance, a sublingual or boccal insert, and anesthetizing hot water bottles, ice packs and cushions are disclosed.

Another important feature is a transparent layer, such as a film or transdermal patch, that, while cosmetically pleasing, enables topical anesthesia of the skin, to eleviate pain or prepare for minor surgical or laser procedures, hair removal, needle stick, i.v.s, etc.

DRAWINGS

FIG. 1 illustrates a view of a fiber on a much enlarged scale in which a drug is dissolved while FIG. 1a shows a small section of the fiber in a still more enlarged scale;

FIG. 2 diagrammatically illustrates a portion of the fiber magnified still more;

While FIG. 2 illustrates a spinnerette for forming the fiber.

FIG. 5 illustrates a bandage or compress formed of the non-woven of FIG. 4, while

Figure 9:
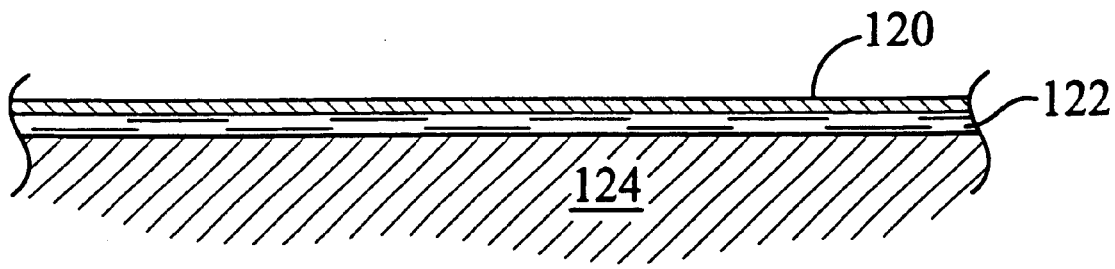

FIG. 9 diagrammatically shows a compress according to the invention.

Figure 10:
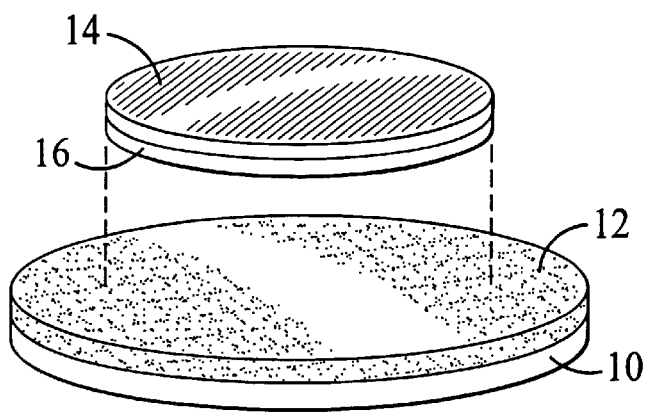
Figure 10A:
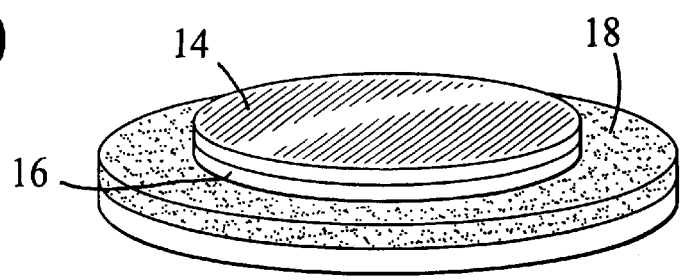
Figure 10B:
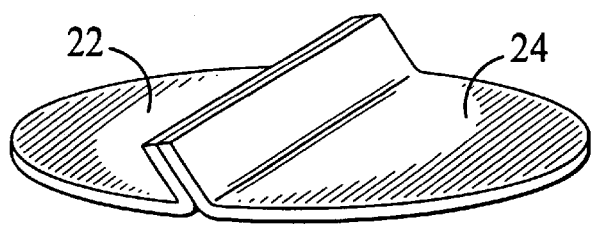
Figure 10C:
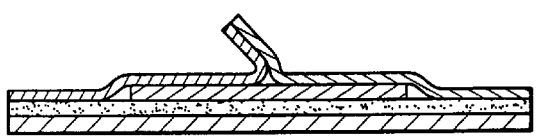
Figure 10D:
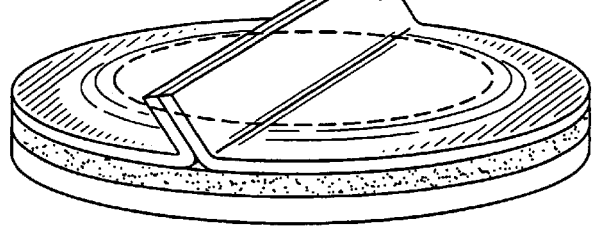
Figure 10E:
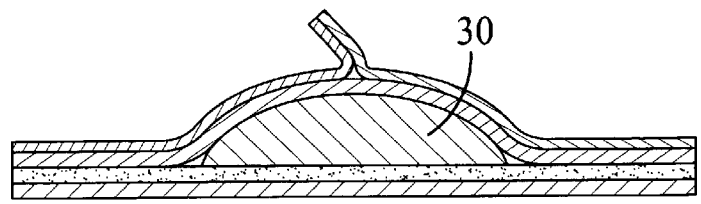
Figure 10F:
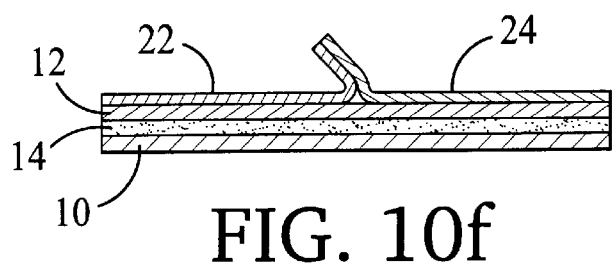
Figure 11:
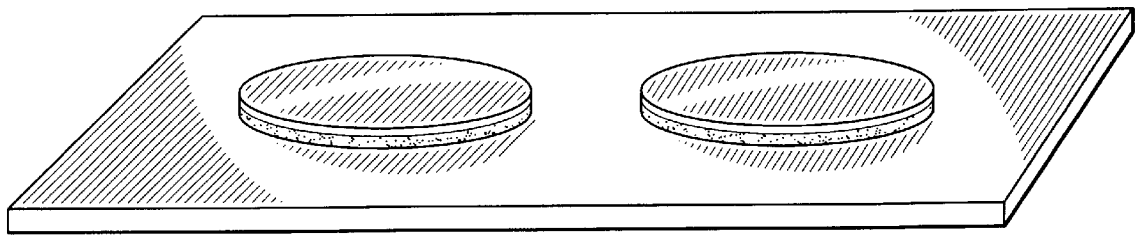

FIGS. 10–10d illustrate various stages in the manufacture of a transdermal patch, while FIGS. 10e and 10f illustrate alternative constructions;

FIG. 11 illustrates the presentation of a series of patches on a continuous sheet of release liner while FIG. 12 illustrates an elongated layer of anesthetic plastic presented in roll form.

FIGS. 13, 14 and 15 are diagrams illustrating alternative techniques for applying a plastisol coating to a substrate, for use in forming such products as are shown in FIGS. 10–12.

The drawings and descriptions of the above-referenced published patents and applications are also incorporated by reference.

DESCRIPTION OF EMBODIMENTS

In an important embodiment, propafenone base in effective quantities is dissolved or otherwise incorporated in a resin, and especially a hydrophobic, thermoplastic resin, in a manner adapted for exposure to the body under conditions in which propafenone in the resin is gradually released into the bloodstream. In one case, in the course of manufacture, propafenone is dissolved in orally administratable solid granules such as coarse or fine powder of non-biodegradable thermoplastic resin. The drug passes through the wall of the gastric tract and into the blood stream. The blood flow then transports the released propafenone to the site at which the drug is effective, e.g. to reduce, treat, or block arrhythmia. In another embodiment, the resin is formed on or as an implant to release the drug directly to heart tissue or the blood stream, or as a transdermal patch or as a drug-applying ear or nose plug. (In the foregoing embodiments lidocaine can be substituted for propafenone.) For demonstration of solubility in resin, propafenone base has been dissolved in a concentration of 50% by weight in intermediate molecular weight polyvinyl chloride, and in concentration of 10% in chlorinated polyethylene. In this and other systems described, when resins are employed in which the solubility of the selected drug is relatively low for the particular therapy desired, a high molecular weight polymer can be selected to provide a higher processing temperature and longer period for the manipulation of the resin and drug in a mill or other processing machine, without degradation or volatilization. These conditions increase the amount of drug that can be incorporated in the resin without degrading the resin, and the relative rigidity of the resin can assist in its grinding to form granular particles or powders.

In one approach the carrier is adapted to provide sustained release in portions of the body where propafenone base or lidocaine base is exposed to alkaline conditions, for instance in the lower intestine. The carrier may reach the lower intestine by oral administration and passage through the stomach. It may be coated with a time-dissolvable or acid-dissolvable protective layer that protects the base form of the drug as the material passes through acidic regions of the gastric system. For this purpose the PVC or other thermoplastic material in which the drug is dissolved may be in the form of orally administered granules in which the propafenone or lidocaine is dissolved, the granules being covered with the protective coating.

An outer layer or protective coating may contain propafenone or lidocaine base which is converted into effective quantities of propafenone or lidocaine chloride during passage through acidic regions of the stomach.

In another case, the concentration of the propafenone or lidocaine dissolved in the PVC itself may be greater near the surface of the granules, or otherwise disposed so that some of the propafenone or lidocaine is removed while exposed to acidic conditions, but an effective concentration remains in the granules as the granules reach the lower intestine.

The particular concentrations of propafenone or lidocaine to employ in the resin can be determined once the parameters of the mode of administration have been selected, e.g., selection of the physical form of the delivery carrier and the point and nature of the absorption to be employed. The effective levels of propafenone or lidocaine in the bloodstream for the antiahrrythmia and antiseizure treatments is already known to the medical field.

Figure 1:
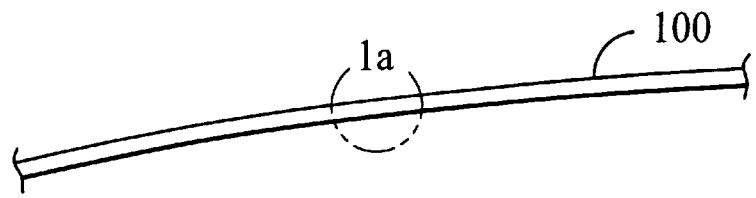
Figure 1A:
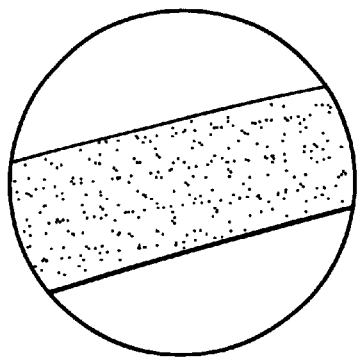

Turning now to the figures, in FIG. 1 a fiber 100 of thermoplastic resin is represented on a much enlarged scale. A small section of the fiber is shown in a still more enlarged scale in FIG. 1A in which stippling denotes anesthetic base or other drugs in solution or incorporated in the resin. Certain fibers of this construction are characterized as having been formed by extrusion and drawing of thermoplastic synthetic resin in which was dissolved a drug having an aromatic ring and which is soluble or capable of otherwise being incorporated in the resin. Other fibers of this construction are characterized as having been formed in similar manner, but of thermoplastic resin not containing the drug. Following forming the fiber, either the fiber per se or when formed with other fibers into a fabric, suture, or the like, the formed device is exposed to the drug under conditions promoting the drug to enter into solution in the body of the fiber. For instance, the drug may be provided in a suitable process solution that promotes entry into solution of the drug into the resin, e.g. in the case of fibers of polyvinyl chloride resin, a 50% lidocaine base in solution with 50% ethyl acetate may be employed.

Figure 2:
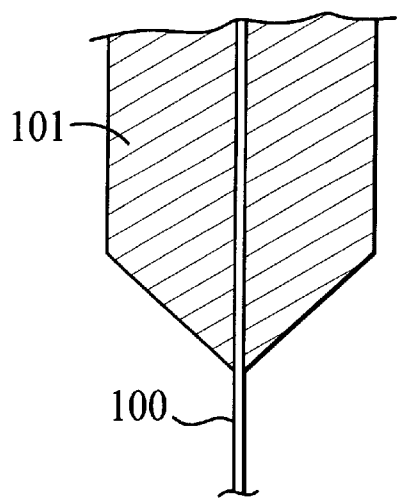

In FIG. 2 a tiny spinnerette nozzle 101 is diagrammatically illustrated from which a fiber 100 is extruded from feed stock comprising a drug having an aromatic ring dissolved in a thermoplastic resin in which it is soluble. Alternatively the fiber may be formed without the drug being in the extruded resin.

Figure 3:
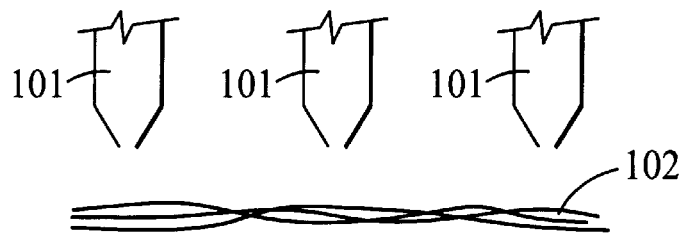
FIGS. 3 and 4 illustrate the process of forming a non-woven using fibers according to FIG. 1.

In FIG. 3 a non-woven fabric 102 is formed by the well known spun bonded process employing spinnerettes according to FIG. 2.

Figure 4:
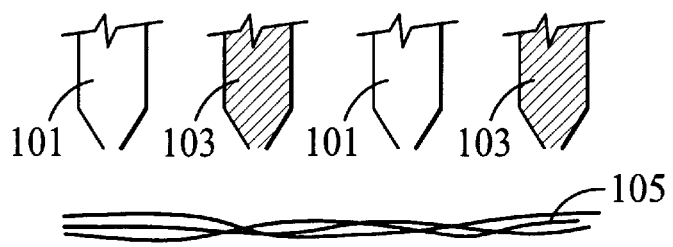

In FIG. 4 a non-woven fabric is formed by the spun bonded process employing spinnerettes 101 according to FIG. 2 and additional spinnerettes 103 from which hydrophilic fibers are extruded, to form a composite non-woven fabric.

Figure 5:
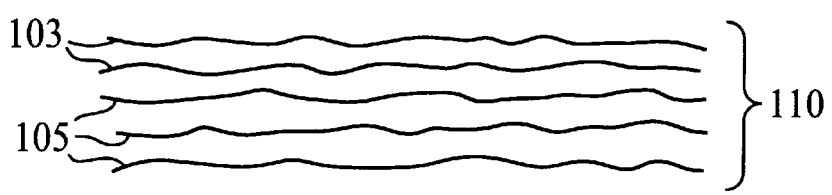

In FIG. 5 is shown a bandage or compress comprised of layers of non-wovens according to FIGS. 1–4.

Figure 6:
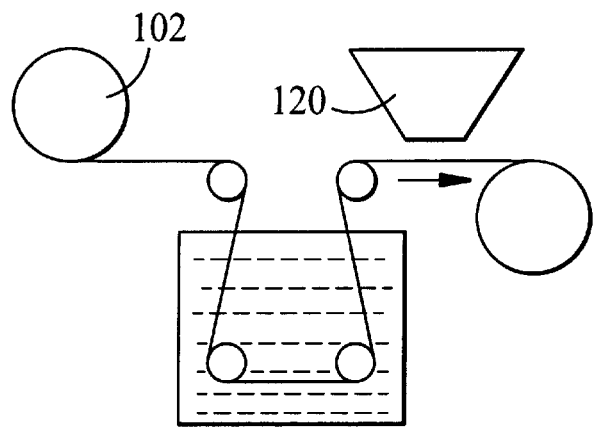
FIG. 6 shows a treatment of a non-woven.

In FIG. 6 is shown the post-forming treatment of the non-woven 102 of FIG. 3 in which drug at the surface of the fibers is converted to water soluble salt form by immersion in a slightly acid bath followed by drying 120.

Fibers, threads, yarns, continuous films or perforated films or strips of plastic resin in which the drug is dissolved or otherwise incorporated may likewise be treated.

Figure 7:
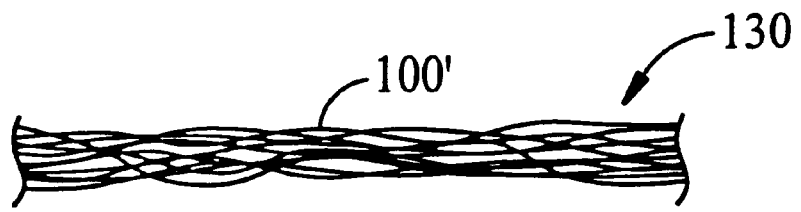
FIG. 7 and 8 show the formation of sutures according to the invention.

In FIG. 7 a suture 130 is shown on greatly enlarged scale formed of filaments according to FIG. 1 that have been subjected to a crimping process to impart knottability to the filaments 100' that comprise the suture.

Figure 8:
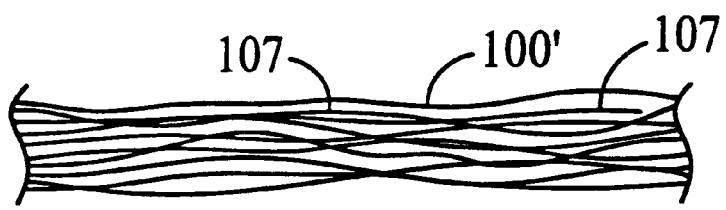

In FIG. 8 a suture is shown formed of crimped filaments 100' according to FIG. 7 and crimped hydrophilic filaments 107.

The sutures of FIGS. 7 and 8 can be formed by coating tensile members, such as silk or glass, with the resin containing the drug.

In FIG. 9 is illustrated a compress 120 containing topical anesthetic associated with an ointment 122 that serves as a transfer layer for the anesthetic from the compress to a healing surgical site 24.

Preferred embodiments of the compress are an assemblage comprised, at least in part, of thermoplastic resin components in which an anesthetic base is dissolved or otherwise incorporated or in which a drug of similar structure in base form, having healing properties, is dissolved.

The thermoplastic resin containing the drug serves as a long term reservoir to dispense the drug to an ointment, from which the drug is transferred to the body. Preferably the ointment contains a surfactant or other agent that promotes penetration of the skin, to aid in passage of the drug. The ointment itself can contain anesthetic in base form, and may advantageously contain an emulsifier where both oily and watery constituents are present. The ointment may contain a mixture of lidocaine hydrochloride and prilocaine base.

Certain embodiments of this aspect of the invention have one or more of the following additional features.

The compress is formed of a bat of fibers at least some of which are thermoplastic fibers in which the drug is incorporated or applied. The bat of fibers includes hydrophilic fibers. Alternatively, a bat of hydrophilic fibers carries a deposit of resin containing the drug, as by printing an array of dots or a reticulated pattern of lines, between which areas of hydrophilic fibers are exposed. Alternatively the compress is formed of a non-woven fabric of fibers at least some of which are thermoplastic fibers in which the drug is incorporated. The non-woven fabric includes hydrophilic fibers. And in still another alternative, the compress includes a gel or gel-like substance that includes a constituent comprised of hydrophobic thermoplastic in which the drug is incorporated. The constituent may be a film, shredded film, fiber or granules of the thermoplastic in which the drug is incorporated.

In still another embodiment, the compress comprises collagen alginate dressing containing powder granules of hydrophobic thermoplastic in which the anesthetic is dissolved.

Benefits of Pain Relief System of the Invention and Further Examples

The invention has very important advantages for dermatology and dermatological surgery, and for taking skin for graft purposes, and has very wide applicability in general surgery, and surgery of other specialties.

One important aspect of the invention concerns preemptive anesthesia. Medical research has indicated there are benefits in employing presurgical local anesthesia even in cases where general anesthetic is to be administered for blocking the central nervous system. It has been shown that concurrent local anesthesia avoids shock to the peripheral nervous system, promotes healing, and helps avoid persistent sensitivity of the surgical area after healing has occurred. The products described can have a desirable pre-emptive anesthesia effect. Local anesthesia during the painful recovery period achieved with the same products can likewise reduce sensitivity of the eventually healed area.

The pre-emptive effects and many other benefits of prolonged local pain relief using the novel topically anesthetizing plastic are illustrated by the following idealized scenario.

Scenario

The patient is examined using an endoscope that has an anesthetizing covering formed following the teachings of the invention.

A patient is scheduled for surgery. Under physician's instruction, the patient, at home, applies an anesthetizing plastic preoperative covering to the face, chest, abdomen, back or other area where the surgery is to occur.

This is done simply by pressing a self-adherent or otherwise secured film, sheet or foam of anesthetizing plastic upon the skin, or by applying a fluid composition that forms a long-acting anesthetizing film, or by applying a cream or coating containing fine anesthetizing plastic particles, such as solid PVC particles, in which the drug is present in solid solution or is otherwise incorporated.

The patient arrives at the hospital with the surgical site numb.

Prior to surgery, without pain, blood samples are taken or injections are made with needles in the anesthetized area of the patient.

Also, prior to surgery, the patient is prepared for general anesthesia by having an endotracheal tube placed in the trachea. Both the tube and the film-formed cuff of the endotracheal tube have anesthetizing plastic surfaces exposed to the tracheal tissue which numbs very rapidly.

General anesthesia is then administered to the patient, but a relatively light level can be used, and dosage of muscle relaxants can be limited, because of the topically anesthetizing endotracheal tube. Anesthesia of the tracheal tissue assures the anesthesiologist that the patient will tolerate the tube throughout the surgical operation and during recovery. Following the surgery, the light level of general anesthesia and limited use of muscle relaxants, made possible by the anesthetizing tube and cuff, results in faster awakening of the patient and fewer side effects.

During surgery, one or more flexible anesthetizing drain tubes, strips, threads, rods or devices appropriate to the surgical site are temporarily implanted in proximity to nerves that have been disturbed. This may be done e.g. in the posterior gutter of the chest or next to nerves in the peritoneal space or the peridural space, etc.

Under the closed incision the surgeon leaves an anesthetizing drain tube or an anesthetizing strip, rod or fiber. The surgeon employs sutures that have an anesthetizing exterior, and applies an anesthetizing absorptive compress upon the closed surgical site.

During recovery the patient can tolerate the deep pain produced by the surgery and the presence of foreign devices without heavy doses of morphine or similar sedations, because of the action of these devices.

As a result, during recovery, the patient remains alert, rapidly re-establishes normal bodily functions, and requires less attention by hospital staff than has often been the case.

In many cases the patient can be sent home early, as the incision is relatively pain-free. Implanted anesthetizing devices are left in the patient's body when the patient goes home, to be removed later when the anesthetizing sutures are removed. During convalescence anesthetizing plastic hot compresses or hot water bottles, ice packs and foam cushions are employed.

The sutures and the drains, strips and other devices that were left in the body are removed by tension applied to the devices. Fiber reinforcement in the devices assures that the devices do not break. Because of their continued anesthetizing effects, little pain is experienced as the devices are withdrawn, even if adhesions have begun to form.

In some cases, for instance in the case of pancreatic cancer, permanent or semi-permanent anesthetizing implants of selected shape are left in the body long-term to ease the pain of the patient.

The skin over the healed incision is not sensitive due to the strategy of employing pre-emptive local anesthesia combined with general anesthesia.

Prolonged local pain relief products realized according to the invention thus have many roles to play in surgery.

Other uses in the fields of allergy, anesthesiology, burn treatment, cardiology, dentistry, dermatology, gastroenterology, neurology, oncology, orthopedics, pediatrics, podiatry, urology, veterinary medicine and numerous other branches of medicine and personal care are illustrated further below and in the referenced patents and applications, or will be apparent to those of ordinary skill.

HOME AND PERSONAL USE

The cook with the burned finger applies an anesthetizing plastic strip and proceeds to complete dinner preparations, as the pain subsides.

A child cries "Mommy I have an itch". A spot-size, adherent, non toxic anesthetizing plastic bandage, made pursuant to the invention, is applied with a kiss and the child's discomfort is soon relieved.

The child with a bad scrape has an anesthetizing plastic strip applied and returns to play.

The athlete applies an ice pack or a water bottle having an anesthetizing outer covering.

DEMONSTRATIONS

As indicated above, lidocaine base and other anesthetic bases of amide type and ester type have been shown to act as plasticizers of PVC and other plastic resins such as CPE (chlorinated polyethylene) and EP (ethylene propylene). Both EP and CPE have been processed to hold about 25% lidocaine base by milling, while PVC has been processed to hold about 50% of lidocaine base. The polymers release lidocaine to their surface to produce a prolonged anesthetic effect. The rate at which migration occurs varies from plastic to plastic, a phenomenon which can be used to advantage to establish the proper drug delivery rate for the desired application.

Anesthetic bases also demonstrate marked solubility in many acrylic polymers and serve in high concentrations to make the composition tacky as an adhesive that is employed to place the anesthetizing plastic reservoir material in close conformity to the skin.

Most of the following demonstrations employ PVC (fully polymerized polyvinyl chloride) and lidocaine base, both of which are FDA approved products, known for their biocompatibility under many conditions such as medical tubes and skin patches. Likewise, methacrylates are approved for instance as bone cement and for topical adhesives, as are acrylic resin adhesives.

Solvent-based articles have been fabricated employing solutions of PVC, as well as other resins, and lidocaine base in process solvents such as THF (tetrahydrofuran), cychlohexanone, and toluene. These solutions, containing the plastic resin and lidocaine, have been printed or painted on cotton gauze, and on the exterior of silk suture, vinyl endotracheal tubes, Foley catheters, naso-gastric tubes and other devices to provide bodily tolerance to these articles. The process solvents are removed by evaporation leaving the anesthetic incorporated in the polymer layer.

A use of such a solvent-based coating system is the coating of large concentrations of local anesthetic base in methacrylate plastic upon a carrier backing to provide anesthetizing patches for the skin. In cases where the carrier backing is PVC, the backing serves as a reservoir and the adhesive coating can be thin as its function is only to serve as an adherent and transfer layer, and not as the principal reservoir or as a metering layer.

As another manufacturing approach, in many cases found to be better than solution coating, useful products have been produced in a milling operation by combining lidocaine base with PVC between two hot rollers, with the addition of heat stabilizers to prevent discoloration at 340° F. during milling. Both E.P.O. (soy) and Ca—Zn heat stabilizers, which been employed, are F.D.A. approved for medical devices.

Laboratory demonstrations using these and other methods of application have shown that lidocaine base and other amide and ester type anesthetics, in sufficient concentrations, are potent plasticizing agents for polyvinyl chloride and other plastic resins. For instance, lidocaine added to polyvinyl chloride is all that is needed to create a soft, stretchy, elastic vinyl milled film or sheet. Like the common vinyl plasticizer di-isooctyl phthalate, lidocaine base slowly migrates to the surface of the formed object, to serve as a sustained source of anesthetic to tissue contacted by the device. The rate of drug delivery is governed by the selected concentration of the drug, the selected plastic resin and the acceptance rate of the part of the body with which the anesthetizing plastic is in contact. In the case of lidocaine, upwards of 50% by weight in solution in PVC can be employed. A piece of such milled vinyl anesthetic material has remained taped to skin for 10 days without any diminution of anesthetizing effect or apparent loss of plasticization.

With PVC-lidocaine products, topical anesthesia is provided to any mucous membrane or body cavity lining within five minutes by an article constructed of a 50%—50% by weight PVC-lidocaine base composition. With this system, adult skin requires between one and two hours of direct contact for onset of anesthesia, depending upon the type of anesthetizing plastic selected, presence of enhancers, and surface preparation. Numbing of the skin (hypesthesia) is found to be accelerated by the action of penetration promoters. For instance, if the skin is first washed with an enhancing agent such as lauryl alcohol, oleyl alcohol, ethyl oleate, or nonionic surfactants such as dimethyl lauramide, faster onset is achievable. Wiping with isopropyl alcohol and application of scrub cleansers such as Betadine scrub, which contains surfactants, can speed drug penetration of the unbroken skin.

Process solution techniques of applying the drug in solution to a PVC substrate, or a drug-PVC composition to PVC or other substrates are applicable to pre-formed objects and carrier sheets, by simple coating, painting or spraying techniques.

Milling has the advantage over such process solution techniques in not requiring volatilization of a process solvent. Products similar to milled products can be produced by die extrusion techniques in cases where sales volume warrants the investment or in cases where tube or other profiles are desired. Vinyl and lidocaine withstand the temperatures and shear forces associated with milling and extrusion without breakdown or detrimental reaction. The cooled product is found to be flexible, biocompatible and efficacious.

By mixing solution grade PVC powder and lidocaine as by a Henschell mixer, it is found that a sufficient temperature may be achieved under mixing conditions to enable the lidocaine to enter into solution in the PVC without reaching the melting point of the lidocaine or the PVC. Under such conditions an anesthetic base-PVC combination possesses the advantage of not requiring a heat stabilizer in processing.

It has been further discovered, however, that a plastisol approach in many instances offers important advantages over the other techniques. To achieve a low temperature plastisol a low concentration of a suitable alcohol is included to form a plastisol composition, for example the plastisol is formulated with lidocaine base, polyvinyl chloride and an alcohol such as lauryl or oleyl alcohol.

Also for a low temperature plastisol, a composition can include prilocaine in combination with lidocaine and PVC. Lidocaine base (a crystalline white substance at room temperature) is very soluble in prilocaine base (an oily liquid). A 50%—50% oily liquid eutectic mixture forms a pourable plastisol when mixed in equal amounts with solution grade PVC, with no other ingredients. Prilocaine has the potential disadvantage of producing methemoglobinemia in large systemic dosage. In many circumstances it is not expected that blood levels would prove to be dangerously high with topical anesthetic devices fabricated by this technique. A similar "eutectic" mixture of tetracaine and lidocaine is also effective.

A plastisol formed with the combination of lidocaine and one of the alcohols just mentioned, and PVC of solution grade, or with prilocaine or tetracaine as mentioned, is screen printed on cotton surgical gauze and then heated to about 275°–300° F. briefly to form a spot form or other pattern of anesthetic coating. The gauze portions not coated provide for absorption of blood and exudates; the printed pattern of congealed anesthetic plastisol alleviates pain from a surgical incision, laceration, or burn.

Lidocaine-PVC plastisols also are utilized to create pain relieving devices as when the plastisol is molded to form the device or is coated on a preformed device. A vinyl penrose surgical drain coated with the plastisol, and suitably heated to congeal the plastisol, can be positioned in an abdominal incision to relieve pain mediated from sympathetic pain endings in the peritoneum. A chest tube coated on its distal 4 inches can be positioned to keep intercostal nerves anesthetized post thoracotomy. A Foley catheter coated with an anesthetic plastisol can relieve catheter discomfort. A drainage tube formed entirely of the plastisol is formed by coating the plastisol on a tubular mold, heating the plastisol to congeal it, and stripping the tube from the mold by a rolling action.

A plastisol pain control device is extruded as a layer around a polyester, silk, or glass thread and heated to form a strong composite fiber for placement in the peridural space. The internal fiber provides tensile strength for enabling removal by application of tension to the portion of the device remaining out of the body. Sutures (such as silk) coated with a PVC-anesthetic plastisol reduce pain while in place and during removal. Early discharge of the patient can be made easier to accomplish if skin and sympathetically mediated pain is relieved or eliminated for several days subsequent to major surgery by such devices.

PLASTISOL EXAMPLE I

An anesthetic-plastic plastisol is created using oleyl alcohol as a dispersant as well as plasticizer. The alcohol disperses the aggregated PVC particles and the lidocaine particles and brings them into intimate contact with each other.

A mixture of 15% by weight oleyl alcohol with 42.5% by weight lidocaine base and 42.5% by weight emulsion grade polyvinyl chloride, is formed by adding the alcohol after a mixture of the latter two ingredients is heated to about 340°–350° F. With grinding, stirring and persistent agitation a fluid is formed that is painted on an aluminum foil and placed in oven. A film is created at 300° F. in about 2 or 3 minutes. The film is tough, elastic and stretchy and has marked topical anesthetic properties over a period of time when applied to the skin. In similar fashion the plastisol is knife coated to a uniform thickness upon a substrate, followed by heating to congeal the resin. In another case, the plastisol is poured into a mold to provide a product of a desired functional shape.

PLASTISOL EXAMPLE II

The plastisol of Example I is formed into a cord, a tube and a penrose drain by forming a sheet and heat sealing it to form a tube or solid cylinder.

A tube is formed by painting the plastisol over a piece of glass tubing that serves as a mold. The painted mold is heated by heatgun or oven to congeal the plastisol and the resultant tubular layer is then stripped by rolling from the mold to provide a thin-walled tubing for use as a drain. The tube is useful for instance to drain the peritoneum and provide anesthesia at the sympathetic nerves related to the peritoneal cavity.

The plastisol is also injected with a syringe into a section of silicone tubing. The silicone tubing is placed in the oven at 300° F. to cure the plastisol. The tube is removed by cutting with a sharp instrument, and the remaining central core of cured anesthetic plastic plastisol comprises a flexible anesthetic rod or cord depending upon the size of the mold tube.

PLASTISOL EXAMPLE III

A Foley catheter of vinyl is painted with the plastisol of Example I and cured by application of heat with a heat gun that heats the superficial areas of the device without damaging the structure of the catheter.

Application of the plastisol to a preformed object made of vinyl provides compatibility of materials that ensures a good bond.

For applying the plastisol to preformed objects of other materials, an intermediate layer, e.g. a thin layer of methacrylate adhesive, is applied to achieve better bonding of the anesthetizing plastic.

Reinforced rods or fiber are created by first pulling glass fibers through a section of silicone tubing, subsequently pumping the plastisol of Example I into the tubing and curing the assembly with heat. The curing PVC-lidocaine plastisol binds to the glass as the result of applying a roller to the exterior of the silicone tubing to assure that the plastisol is thoroughly integrated into the pores of the glass fiber. The resultant rod or fiber has tensile strength that enables it to be removed from the body by application of tension.

PLASTISOL EXAMPLE V

The plastisol of Example I is screen-printed as an array of spaced spots on a cotton gauze square and cured with heat. The gauze square has anesthetizing properties. Placed over a wound it numbs tissue while absorbing fluids from the wound.

PLASTISOL EXAMPLE VI

A plastisol is made of a mixture of 25% prilocaine, 25% lidocaine and 50% polyvinyl chloride, by weight. The combination is a thick liquid that is readily paintable or applied as coating or used as a silk screen printing fluid. In the example it is painted on selected objects and heat cured to form a very tough tenacious coating that is very easily handled. The resultant product has excellent topical anesthetizing properties.

PLASTISOL EXAMPLE VII

Foam is formed from the plastisol of Example I by adding between about 2½ to 5% foaming agent, such as sodium bicarbonate, to the plastisol. The concentration of foaming agent is selected in accordance with the desired foam density. The plastisol is cured by heating to 350° F. as before. To prevent discoloration it is advantageous to add 1 or 2% of zinc calcium heat stabilizer or soy stabilizer.

Resultant foams range from very hard to relatively soft. Other blowing agents, such as halogen compounds, are also used to form anesthetizing plastic foams.

As with the preceding example, various forms of anesthetic base-PVC combinations lend themselves to foaming with sodium bicarbonate and other blowing agents. Foams with a well formed outer surface establish skin hypesthesia rapidly and provide a mechanism for providing uniform compliant skin contact. Foams formed at relatively high temperatures typically require heat stabilizers in their composition. They can be formed with lidocaine-alcohol PVC plastisols or lidocaine-prilocaine-PVC plastisols or they can be formed by milling techniques.

PLASTISOL MOLDED FOAM EXAMPLE VIII

The plastisol of Example I or the plastisol of Plastisol Example VI is made into a molded foam object by the technique described in Plastisol Foam Example VII. When sodium bicarbonate (or other foaming agent) and heat stabilizer are added to these plastisols, foam is produced at about 350°. A starting layer a few thousandths of an inch thick expands remarkably to between 5 and 10 times its preheated thickness.

The plastisol or mixture is poured into a mold of selected shape and heated to cause foaming to fill the mold and produce a foam shape of anesthetizing plastic as determined by the mold. This technique is employed with molds suitable to form drug delivery or anesthetizing plastic articles. These include foam ear plugs, foam nose plugs, or foam rectal or vaginal suppositories, sublingual or boccal inserts, cushioned surfaces for prostheses, and other foam objects comprised of anesthetic plastic foam or drug delivery plastic foam.

PVC anesthetic base devices are not intended for total absorption or to be metabolized by the body. However, by introducing a length of a suitably sized tubing, rod, fiber or molded plastisol device next to pain conducting nerves, prolonged blockade of those nerves can be effected for hours, days, or weeks. The emergent end of the device can be secured with adhesive tape and removed painlessly when appropriate. Techniques for introducing a fiber in the body are well established (utilizing endoscopic, large bore needle or open surgical techniques).

FURTHER PLASTISOL EXAMPLES IX

A set of further examples illustrates the range of concentrations of anesthetic that can be employed using plastisol techniques, and conditions of manufacture and use.

In these examples a plastisol was prepared by mixing powdered polyvinyl chloride (emulsion grade), with a fluid comprising either (a) a single anesthetic base in combination with isopropyl alcohol, (b) a non-alcohol mixture of two topical anesthetic bases, the mixture having a lower melting temperature than either of the anesthetics alone, (c) a water suspension of an anesthetic base or (d) a solution of anesthetic base and lauryl alcohol. All transdermal patch examples were applied to the arm of a white adult male.

The first set of examples 1–5, employed the single topical anesthetic, lidocaine base, combined with polyvinyl chloride and isopropyl alcohol.

EXAMPLE 1

60 grams lidocaine base and 120 grams PVC powder were combined by mixing in a household blender with 300 cc's by volume isopropyl alcohol. A paintable fluid plastisol was formed (with lowered concentrations of alcohol, mixtures became thicker and less paintable). The fluid was painted upon a plastisol film carrier sheet of PET (polyethylene terephthalate, i.e. du Pont's Mylar) such as is employed in turkey baking bags, with the sheet taped flat to a thin metal carrier plate. The painted sheet was heated to 225° F. for a period of 2 minutes, driving off the alcohol and congealing the powdered resin anesthetic combination. The result was a clear, solid, flexible anesthetic plastic layer on the carrier. The composite was wrinkle free and appeared more pliable than a PET sheet by itself due to a "rubberizing" effect of the anesthetic layer, non-tacky layer that contained 33% lidocaine base. When the anesthetic plastic layer was placed in contact directly with the skin, a superficial anesthetic block was achieved with a 3 hour onset. The block had 15–20 minute persistence after removal. The block attained was sufficient for the subject to withstand a pin prick of the skin without pain. This relatively low concentration of anesthetic is suitable for prolonged use over large areas of skin subject to chronic discomfort, such as burn dressings and treatment of post-herpatic neuralgia and other hypersensitivity skin states as causalgia.

Thickness of the anesthetic plastic layer, hence drug availability over time per unit area, is varied depending upon duration of the effect desired.

A coating containing approximately Lidocaine 25 mg/ 1 $in^2$ is found to produce a numbing block of the skin for 24–36 hours.

EXAMPLE 2

The procedure of Example 1 was followed employing 80 grams lidocaine base, 120 grams PVC, providing a 40%–60% ratio of anesthetic to PVC, mixed with 60 cc's isopropyl alcohol. This formed a very thin paintable plastisol, the less alcohol required being attributable to the higher concentration of the anesthetic base. The plastisol was painted upon a PET carrier sheet according to example 1 and baked at 225° F. for 2 minutes. It formed a solid, flexible, slightly tacky anesthetic plastic layer upon the substrate having contact clarity (slightly translucent). A trace concentration of microscopic precipitated anesthetic crystals was observed. When the coating was held in skin contact it provided a somewhat moderate anesthetic block after 2½+ hour onset, of 15–20 minutes duration following removal of the patch. The block sufficient for the subject to withstand pin prick of the skin without pain. The resultant product is suitable for application to moderately large areas of the skin for treatment, e.g. of chronic discomfort.

EXAMPLE 3

The procedure of Example 1 was followed, using a 50–50 lidocaine-PVC mixture; 100 grams of lidocaine base and 100 grams PVC were mixed with 60 cc's of isopropyl alcohol to form a thin fluid paintable plastisol. The plastisol was painted on PET film and baked at 225° F. for 2 minutes. It formed a translucent, solid, flexible, slightly tacky anesthetic plastic layer upon the carrier, containing 50% anesthetic base. Microscopic precipitated anesthetic crystals were more pronounced than in Example 2. The layer produced a moderate block following a 2½ hour onset, with approximately 15 to 20 minutes duration following removal from the skin. The block was sufficient for the subject to withstand pin prick without pain, and after presence for 12 hours, penetration by No. 23 needle without pain occurred. The block is sufficient to facilitate minor dermatological procedures, such as laser treatments for the removal of hair or cosmetic imperfections.

EXAMPLE 4

The same conditions as Example 3 were employed, but using a polyethylene sheet of 0.0007 inch thickness (food storage bag material). The resulting composite product was more compliant, exhibiting less tensile strength than Example 3, and greater conformability.

EXAMPLE 5

The procedure of Example 1 was employed with a 60 to 40 ratio of lidocaine base to PVC. 120 grams of lidocaine base and 80 grams of PVC were mixed with 60 cc's isopropyl alcohol to form a very thin, fluid plastisol. When applied by paintbrush to PET film upon a metal base sheet and baked at 225° F. for 2 minutes, it formed a translucent, solid, flexible, barely tacky anesthetic plastic layer with a high concentration of precipitated anesthetic crystals. It demonstrated 2¼ hour onset of a moderate block, with 15 to 25 minutes duration following removal. The block was sufficient to withstand penetration with a 23 needle without pain.

Examples 6 and 7, now to be described, employed a mixture of tetracaine and lidocaine that formed an oily liquid at room temperature, a so called "eutectic". No other fluid component was employed.

EXAMPLE 6

A 60% anesthetic, 40% PVC mixture was prepared, the anesthetic comprising equal parts by weight of tetracaine base and lidocaine base so that the ratios of the total were 30% tetracaine, 30% lidocaine and 40% PVC. The three ingredients formed a thick fluid plastisol capable of being applied with a squeegee. The plastisol was applied to a carrier film of PET and baked at 250° F. for 2 minutes. It formed a clear, solid, flexible anesthetic plastic layer having a tacky surface with microscopic eutectic fluid at the surface. It produced a profound block with 1½ hour onset. Penetration with a No. 23 needle occurred without pain. Duration of the block after removal of the transdermal patch was one hour. Slight reddening of the skin that occurred was useful to mark the anesthetized area for the procedure following.

The depth of block and duration were sufficient to facilitate dermatological procedures, such as needle aspiration biopsy, laser removal of skin lesions and hair removal, as by laser, waxing or electrolysis.

EXAMPLE 7

The procedure of Example 6 was followed, except that the carrier sheet was polyethylene film and the mixture was 50% anesthetic to 50% PVC, employing 33% tetracaine base and 17% lidocaine base, by weight in a "eutectic" mixture. This formed a thick fluid plastisol and was applied with a squeegee to the polyethylene film and baked at 250° F. for 2 minutes. It formed a slightly translucent (contact clarity) solid flexible anesthetic plastic layer that was slightly tacky, with some precipitated anesthetic crystals. It demonstrated a profound block within 1½ hour, suitable to withstand penetration by a No. 23 needle without pain. The block lasted for one hour following removal of the patch, with some reddening of the skin observed.

EXAMPLE 8

To a dry mixture of 50% lidocaine base, 50% PVC, was added water in a household blender and 30 cc of Betadine Scrub (a commercial surgical antiseptic cleansing solution containing povidone-iodyne and lauramide DEA, available from The Purdue Frederick Company, Norwalk, Conn.).

Sufficient water was introduced to produce a frothy, paintable suspension. The suspension was painted upon a PET sheet and baked at 250° for five minutes.

A congealed, slightly tacky coating was produced which was translucent but demonstrated substantial contact clarity when pressed upon the skin, the coating having a slight yellowish hue attributable to the Betadine. The results were similar to Example 3.

The examples so far described that employ isopropyl alcohol or water to form a plastisol depended upon volatilization of the alcohol or water during preparation and in the baking such that none remained and the PVC congealed to form a continuous coating. When using this system to form a thick layer or object, a degree of porosity of the product can be obtained, which in certain circumstances can be advantageous. Blowing agents can also be employed when porosity or foam is desired.

In the case of employing anesthetic mixtures that are liquid at room temperature, no volatilization occurs and the plastisols can be produced in thick layers or molded forms without porosity.

Other examples of useful plastisols employ suspending fluids that do not volatilize during baking and permit forming articles with significant thickness without porosity. Examples of such fluids are olyl and lauryl alcohols. Lauryl alcohol is found to be highly compatible with PVC and is employed in the following examples.

EXAMPLE 9

A plastisol comprised of 20% lauryl alcohol, 40%. lidocaine base, and 40% PVC, by weight, were mixed to form a paintable fluid. The plastisol was painted upon a PET carrier sheet and baked as in Example 1. Results similar to those of Example 2 were obtained. Multiple anesthetic plastic layers can also be formed with heating between applications. The results are given in the following table:

assembly was placed in an oven and heated to 225° F. for approximately 5 minutes. The resultant member was a flacid, congealed rubbery sheet, ⅛ inch thick, approximately 8 inches by 5 inches in breadth, from which all of the objects were readily released. In the instance of the coins, extremely thin films were formed beneath the coins, the film material exactly replicating the negative shape of the face of the coins and their edge knurling. Likewise, detailed impressions of the safety razor and scissors were formed.

Similarly, as has been previously described, deposition or molding of foams and printing of plastisols on compresses, bandages and the like can be prepared.

EXAMPLE 12

Transdermal patches were formed with the material of Examples 1 through 9 and applied directly to the skin, held in place by a pressure sensitive adhesive border that surrounded the anesthetic patch. The border was provided by an overlying sheet that extended beyond the dimensions of a segment of the plastisol coated film. In other cases a separate pressure-sensitive adhesive tape was employed to secure an anesthetic segment against the skin.

EXAMPLE 13

Examples similar to Example 12 were prepared, with the adhesive also containing anesthetic, to avoid pain during removal from hairy skin, and the like.

| Example | L | T | PVC | % Anesthetic | Added Fluid | Type of Plastisol | Clarity | Crystal Conc. | Time of Onset | Persistence Minutes | Block |
|---|---|---|---|---|---|---|---|---|---|---|---|
| 1 | 60 g | | 120 g | 30% | alcohol 300 cc | thin | clear | none | 3 hr | 15–20 | pin prick |
| 2 | 80 g | | 120 g | 40% | alcohol 60 cc | thin | transl | slight | 2 ½ hr | 15–20 | pin prick |
| 3 and 4 | 100 g | | 100 g | 50% | alcohol 60 cc | thin | transl | mod. | 2 ½ hr | 15–20 | pin prick |
| 5 5 | 120 g | | 80 g | 60% | alcohol 60 cc | thin | transl | high | 2 ½ hr | 15–25 | #23 needle |
| 6 | 30% | 30% | 40% | 60% | none | thick | clear | none | 1 ½ hr | 60 | #23 needle |
| 7 | 17% | 33% | 50% | 40% | none | thick | clear | slight | 1 ½ hr | 60 | #23 needle |
| 8 and 9 | 40% | | 40% | 40% | 20% lauryl alcohol | paintable | | | | | |
| 10 | 42% | | 42% | 42% | 16% lauryl alcohol | thick | | | | | |

EXAMPLE 10

A brass tube mold form was covered with starch powder. Three coatings of the plastisol formed in Example 9 were applied to the mold form with heating of each coating before applying the next. Heating was by air from a hot air gun, estimated to have a temperature of 225° to 250° F. After the three successive coatings were applied and successively heated, the resulting tubular plastic article was removed from the brass tubular mold by rolling off. The result was a highly flexible, soft tube of approximately ½ inch diameter having a wall thickness of approximately 0.040 inch, suitable for use as a penrose drain. Anesthetization of tissue of the patient with such a tube in place can reduce or eliminate pain during recovery and during removal of the drain tube by typical pulling from the wound.

EXAMPLE 11

The moldability of a material in numerous forms was demonstrated. A plastisol of 16% lauryl alcohol, 42% lidocaine base and 42% PVC was mixed to form a moldable thick fluid. The fluid was poured upon a plate. A number of elements was placed upon the fluid: a safety razor blade, coins of a variety of shapes and surgical scissors. The To form such an assemblage, a film carrier sheet such as PET or polyethylene is coated with adhesive that contains the anesthetic. A segment of the material described in any of the examples 1 through 9 is then deposited upon the adhesive sheet, leaving margins of the adhesive sheet exposed, to which is then applied a release sheet.

In preparing an adhesive carrier sheet or adhesive tape it is preferred to employ a cross-linked acrylic adhesive, such as Monsanto 1753 adhesive, mixed with 15% by weight lidocaine base or 10% tetracaine base. The 1753 Monsanto adhesive contains a solvent that maintains the mixture in liquid form prior to application. The adhesive is painted on the carrier sheet, e.g. PET or polyethylene film and baked as previously described. This results in an adhesive carrier sheet that is entirely clear; i.e., the anesthetic is in solution in the adhesive residue after evaporation of the solvent, and provides an anesthetizing pressure-sensitive adhesive sheet or tape. For forming transdermal patches, a pre-formed segment of the material of any of the examples 1 through 9 is applied to a central area of the adhesive carrier sheet or tape and, after application of release paper to the borders extending beyond the plastisol segment, an outline is cut or stamped to form the final patch, which is then appropriately packaged and sterilized.

EXAMPLE 14

In preparation for application of a patch, a sponge was prepared comprising 1 cc of epinephrine (1:1000, in water) and 1 cc of Betadine scrub. The sponge was packaged in a vapor barrier pouch. Prior to application of an anesthetic patch as previously described, the sponge was removed from the pouch and used to scrub the receiving area. The onset of the block was accelerated by this treatment, while any reddening propensity of the anesthetic was markedly reduced.

EXAMPLE 15

An example of use of the sponge of Example 14 and an anesthetic patch is in needle aspiration biopsy. For instance, for taking tissue from enlarged thyroid, 1½ hrs prior to the procedure, the skin in the lower neck region, over the thyroid, was swabbed with the Betadine-epinephrine sponge and allowed to dry. Segments of anesthetic plastic sheet fabricated according to Example 6 were placed upon somewhat larger adhesive sheets according to Example 12, to form transdermal anesthetic patches. The patches were approximately 1 in. square overall, with the anesthetic plastic segments approximately ¾x¾ in. Four of these patches were applied over the thyroid on one side of the neck. 1½ hours later the skin in areas beneath the anesthetic plastic segments were totally blocked. Slight redness of the skin, an effect of the tetracaine, remained at the sites of the anesthetic segments, serving as markers for the attending physician and pathologist.

Needle aspiration biopsy was then performed, with No. 23 needle inserted in the areas of slight redness. The patient had no sensation of penetration of the skin with the No. 23 needle.

The degree of redness can be increased if desired, by reducing the concentration of epinephrine in the swab. In other cases, other markers are associated with the patch, such as ridges that leave an indentation in the skin marking the anesthetic area of the patch, transfer dyes, etc.

EXAMPLE 16

A sponge was prepared using a 50/50% mixture of Betadine Scrub and a magnesium hydroxide buffer (Phillips Milk of Magnesia, 80 mg/ml magnesium hydroxide in purified water). The Ph of the mixture was 9.8. The forearm was wiped with the sponge and a segment of the sheet as prepared in Example 6 was applied. The preparation was found to increase the speed of onset and the depth of block. The effect is attributed to the store of residual magnesium hydroxide particles that maintained the alkaline condition during residence of the patch. A moderate block (insensitive to pin prick) was obtained within 1 hour, and by 1½ hours a profound block was obtained, enabling penetration by a No. 23 needle, without sensation. Slight redness was observed. The block lasted for about 1 hour.

EXAMPLE 17

The procedure of Example 16 was repeated with the presence of epinephrine in the Betadine Scrub as described in Example 14. The same rapidity of onset and depth of block was obtained. No redness was observed.

EXAMPLE 18

A plastisol was prepared according to Example 8 (40% lidocaine, 40% PVC, 20% lauryl alcohol) and placed in a receptacle associated with a pressurized aerosol spray. The plastisol was sprayed upon a 4 inch wide strip of PET film using constant relative motion between the film and sprayer. The resulting deposit had a density of 20 mg/in$^2$.

After baking for 2 minutes at 220° F., a clear smooth coating of the anesthetic plastic was obtained.

Testing produced the results reported for Example 8.

The test was repeated with the same result.

This verifies the reliability of a production technique of advancing, for example, a 4" wide PET film substrate past a fixed aerosol sprayer, and advancing the coated substrate through an oven.

EXAMPLE 19

Referring to FIGS. 10–10*d*, the formation of a transdermal patch is illustrated.

A flexible backing layer 10, of, for instance, polyvinyl chloride, polyethylene or polyester, is coated with a compatible pressure sensitive adhesive 12, medical grade, of type commonly employed to secure adhesive bandages or tape to the skin. From this sheet a disc is die cut, of form shown. An anesthetic plastic sheet is prepared in accordance with any of the foregoing examples of example group IX, by application, to a carrier sheet 16 of polyester, a pvc plastisol layer 14 that contains topical anesthetic, followed by heating to congeal the plastisol. As shown, a circular disc of the anesthetic plastic is formed by cutting, of diameter somewhat smaller than that of the carrier disc 10. The anesthetic disc is deposited centrally of the backing disc, on the adhesive layer 12, so that an annular rim 18 of adhesive is exposed, and the anesthetic plastic layer 14 faces outwardly.

A pair of release sheets 22, 24, FIG. 10*b*, e.g. of silicone coated paper, or plastic, are applied to form the assemblage of FIGS. 10*c*and *d*. By grasping the upstanding tabs 26, the release sheet is removed, to prepare the patch for application to the skin.

The patch of FIG. 10*e* is constructed in similar fashion to that of FIG. 10*d*, with the addition of a resilient foam cushion 30 disposed between the adhesive carrier sheet and the anesthetic plastic assembly. When the surrounding rim of adhesive is applied to the skin, the cusion 30 serves to ensure intimate contact of the anesthetic plastic with the skin. This arrangement may be used to advantage in cases of large patches.

The transdermal patch of FIG. 10*f* is also similar to that of FIG. 10*c*, except that the anesthetic palstic plastisol 14 is deposited directly on carrier sheet 10, to serve as a reservoir of anesthetic, and a compatible pressure sensitive adhesive (cross linked acrylic adhesive) 12, such as Monsanto 1753 is applied over the surface of the cured plastisol. The adhesive slay have topical anesthetic base preloaded into it, for accelerating the onset, or natural diffusion may be employed to achieve equilibrium conditions by migration of the anesthetic into the adhesive after deposit.

The patches of FIGS. 10*c* and 10*f* are typically transparent and cosmetically attractive, suitable, for instance to be applied to the nose and face in overnight application in anticipation of laser treatment for removal of hair, scars or vascular capillaries, etc. The patch of FIG. 10*c*. may likewise be cosmetically attractive by choice of a clear resin cushion that is suitably thin.

As shown in FIG. 11, in another form, the patches according to FIG. 10*a* are applied, face down upon a continuous release sheet, which is supplied to the consumer, e.g. in the form of a roll.

In the example of FIG. 12, a central band of plastisol 14 is applied and cured on a carrier sheet 10 of wider width, and adhesive 12 is applied along each side. The carrier sheet 10 and adhesive are compatibly selected to permit release, so that the assemblage is wound into a roll for dispensing, without need for an intervening release layer.

For applying the plastisol to a carrier sheet in production, various techniques can be employed. FIG. 13 illustrates roll coating application of the plastisol 14 to the carrier sheet 16; FIG. 14 illustrates knife coating of the plastisol upon carrier sheet 16; and FIG. 15 illustrates spray application according to the techniques described in example 18.

Among other uses of the patch are the preparation of areas of the skin that repeatedly are penetrated by needles and develop sensitivity. Examples are the accessing of subcutaneous vascular ports, in the injection of botulism toxins to treat blephero spasms (spasms of the eyelid) or dynamic rhytidics (uncontrollable blinking).

Another application is in preparation for administration of local anesthetic block in connection with laser or other cosmetic surgery.

Still other applications include waxing and electrolysis for hair removal.

Tapes, Coverings and Patches

PVC-anesthetic base tapes are simple to form. Tapes with a vinyl component, or tapes coated with acrylic adhesive, can be mechanically coated at room temperature with either a solution of solvent (ethyl acetate)—lidocaine base or an alcohol-lidocaine base solution followed by heat curing. The anesthetic agent is absorbed by the skin and makes the tape capable of numbing skin after contact of an hour or two. Tapes treated with dilute concentrations of anesthetic soluble in the tape structure or its adhesive renders such tapes less painful when removed from hairy or sensitive body areas.

Tapes, and film and sheet coverings may be formed by milling or extruding 50—50 lidocaine PVC compositions as previously described, using plastisols. Such coverings, with or without intervening adhesive or transfer layer, can provide a desired partial numbing effect on burns and areas affected by post herpes neuralgia. Where the coverings are moisture impermeable, retained perspiration on the skin enhances the permeability of the skin to the delivered drug. In such cases, the sheet or tape serves both as the drug reservoir and as the occlusive covering.

A form of acrylic adhesive (available as a spray adhesive from the 3M Corporation) has proven to be useful as a component to demonstrate a device to anesthetize small or large areas of human skin. Lidocaine base has been found to be soluble in high concentrations in the solids component of 3M's #77 spray adhesive, for instance. When the solids component of the adhesive spray (about 30–35% of the spray mixture) is mixed with about 33% lidocaine base, a stable, tacky contact adhesive is formed, due to the effect of the large concentration of lidocaine in the resin. The composition has marked topical anesthetizing properties. The lidocaine acts in a manner similar to its role as a plasticizer to assist in rendering the solids tacky. When the lidocaine concentration in the mixture is increased to 50%, a supersaturated condition prevails, and in a matter of a few hours the excess lidocaine base crystallizes and the adhesive becomes substantially less tacky at room temperature. However, when this adhesive-topical anesthetic mixture is applied to polyethylene film as a carrier and is pressed with a warm hand to human skin, sufficient tackiness is observed that the film clings to the applied areas effectively, but can be readily removed. The tacky product is suitably dispensed with the tacky layer protected by contact with silicone coated release paper.

In another instance a vinyl tape having anesthetic base incorporated serves as a reservoir and a thin layer of methacrylate adhesive applied to the tape serves to adhere the tape to the skin and act as a transfer layer deliver the anesthetic to the skin as it is resupplied by the reservoir.

With such devices, in 1–3 hours topical anesthesia of the skin is established, which will last for 2–3 days if the film patch is left in place. Washing the skin e.g. with lauramide surfactant prior to applying the film decreases the onset time for skin anesthesia. The topical device is easily and painlessly removed with little transfer of adhesive. After removal, anesthesia has been found to be maintained for about 30 minutes. If longer acting anesthetic bases (such as tetracaine and dibucaine) are employed instead of lidocaine, anesthesia is found to last substantially longer following removal. During this interval minor plastic surgery, electrolysis, laser treatment to remove hair, cryosurgery, dermabrasion, or application or removal of tattoos is performed painlessly.

Film patch anesthesia is accomplished with a surprisingly low dose of local anesthetic, about 7 mgs./inch$^2$. A 2 inch×4 inch patch contains about 56 mgs. of lidocaine base, (one gram of lidocaine distributed over one square foot of film). This amount of local anesthetic is found to anesthetize a skin area for about 1 to 2 days. This contrasts with Astra Emlao cream which utilizes approximately 250 mgs. of eutectic prilocaine-lidocaine retained under an inconvenient occlusive dressing.

A number of examples of transdermal patches were described above, under Example IX. Further examples are provided here.

SKIN PATCH EXAMPLE I

A sheet was prepared from a plastisol consisting by weight of 42.5% lidocaine base, 42.5% emulsion grade PVC and 15% oleyl alcohol.

To prepare the plastisol, the three ingredients were stirred with mortar and pestle until homogeneous. The mixture was spread on an aluminum sheet and cured at 300° F. in the oven.

This produced a rubbery, stretchy, tough sheet of clear plastic which over many days became opaque on its surface, but remained flexible.

This sheet was employed as a skin patch by placing a 1 inch square patch on the back of a hand held by a piece of adhesive tape lying over the patch. The product, prepared as a finger bandage, has the center compress layer of a conventional plastic strip bandage replaced by the cured plastisol layer.

When held against the skin for about an hour and a half or two hours, total anesthesia was observed under the contacted area. Onset was accelerated to an hour to an hour and a half by applying Betadine surgical scrub mixture before applying the patch. Betadineo is a mixture of povidone iodine complex in water solution with anionic and ionic surfactants (lauramide DEA).

Such an enhancer can be applied either directly to the skin as a prep before applying the anesthetic plastic layer or dried Betadine® may be provided on the layer itself, which is moistened before applying the patch.

The effect of the scrub solution is to sterilize the surface and to accelerate the absorption of the local anesthetic and the numbing effect. Lauramide enhancers have a similar effect.

SKIN PATCH EXAMPLE II

A film of lidocaine base, PVC and polyethylene oxide (PEO) was prepared. In one case a film of 43% polyethylene oxide, 32% lidocaine base and 32% polyvinyl chloride was prepared by mixing the dry ingredients and placing the mixture in an oven at 300° F. to convert the mixture to a film. In another case a film was prepared with process solvent techniques using methylene chloride and tetrahydrofuran as process solvents. Methylene chloride dissolves the PEO, tetrahydrofuran dissolves the polyvinyl chloride. Both solvents dissolve the lidocaine. After coating, the process solvents were removed by volatilization.

Films formed each way are placed under an occlusive dressing or under a piece of tape, attached as the compress of a finger bandage that has pressure-sensitive adhesive holding strips, or held by other means in constant contact with the skin. Anesthesia develops in 1 to 2 hours. If Betadine® is placed under the film, the onset of anesthesia is accelerated to about 1 hour.

By holding such a film intimately in physical contact with the skin and keeping it covered to prevent loss of moisture, retained perspiration within the skin provides sufficient concentration of water to maintain the hydration of the PEO, and maintain the intimacy of contact between the skin and the film.

As long as the film is kept in contact with pressure, as by pressure sensitive tape, anesthesia is maintained for 10 days.

In other examples, skin patches can employ other water based adhesive systems to hold the solid vinyl drug containing particles intimately to the skin. Such adhesive systems are described in the transdermal patch drug delivery literature.

SKIN PATCH EXAMPLE III

The amount of solids in #77 spray adhesive available from the 3M Company was determined by spraying 100 grams of the solution into a bottle and letting the solvents evaporate overnight. The solids weighed about 35 grams.

The solids consisted primarily of methyl methacrylate with tackifying and other additives.

A solution in methyl-ethyl-keytone and ethyl acetate was prepared of sprayed adhesive solids and lidocaine base in the ratio of 38% lidocaine base by weight and 62% solids of the #77 Spray Adhesive. A paintable fluid was formed by adding sufficient methyl-ethyl-ketone and ethyl acetate to dissolve the solids. The fluid was painted on a polyethylene film carrier sheet with a paintbrush, letting dry between coats by exposing it to heat at 85° F. in a controlled oven.

After 3 coats the product was maintained in the oven at 85° for 24 hours to remove volatiles.

The resulting coating was very tacky, sufficient to adhere well to the skin. The adhesive layer was mounted on release paper in strips 2 inches wide. Patches of this product were applied to the flexor surface and extensor surface of the lower arm of the experimenter and the onset of anesthesia was observed.

This was done under 2 conditions, plain and with preapplication and wiping off of DMSO.

For the plain strip, onset time to establish total numbness of the skin under the patch was about two hours. By rubbing a small quantity of DMSO on the skin first, wiping it off, and applying the patch, the same degree of anesthesia was achieved in about one hour to one hour and a half, depending upon the area to which it was applied. The patch adhered well.

An enhancing effect similar to that of DMSO is obtainable with lauramide DEA-containing compounds, such as the Betadine® scrub of Examples I and II. The polyethylene film and the adhesive layer were removed from the skin very easily without adhesive remaining on the skin.

SKIN PATCH EXAMPLE IV

A solution of lidocaine base 60% and polyvinyl chloride 40% by weight, was dissolved in tetrahydrofuran (THF) and cyclohexanone. This solution was painted on polyethylene film.

A light spray of 3M #77 Adhesive was applied as an intermediate layer to promote bonding to the polyethylene. Then three brush coats of this lidocaine base-PVC 60%, 40% in tetrahydrofuran and cyclohexanol were applied to the polyethylene and dried over a 24 hour period in the manner described in Example III.

This produced a clear non-tacky anesthetic plastic layer adhered to the film. When desired to make it adhere to the skin a light spray of #77 Spray Adhesive was applied and dried for 12 hours. This produced a tacky surface on the layer to which release paper was applied. When applied to the arm in the manner described for Example III, a good anesthetic block was achieved in about 2 to 2½ hours. When DMSO was applied first and wiped off, a good to excellent block was achieved in 1½ hours.

In this example the primary reservoir is the lidocaine-PVC layer. The adhesive serves to hold the reservoir layer intimately to the skin and to transmit the drug from the reservoir layer to the skin.

Fluids, Creams and Lubricious Agents

It has also been found that polymers that display solubility in water and common solvents (for example polyethylene oxide (PEO) combined with a hydrophobic PVC powder in which anesthetic base is dissolved, provides a fluid system, cream or adhesive that can be applied to the skin in water base form, and in the presence of moisture retains its effectiveness. It can be removed with soap and water when desired. Water solubility permits application to hairy areas of the body for treatment of such painful processes as herpes zoster ("shingles") or post-herpes neuralgia.

A similar coating can be applied to a catheter or other medical device and when wetted provides a lubricious and topically anesthetizing surface.

TOPICAL APPLICATION OF PARTICLES EXAMPLE I

For topical fluid application, anesthetic plastic powders are first created. For this purpose a film is formed in an oven at 300° F. employing a mixture of polyvinyl chloride 50% and lidocaine base 50%, by weight. The film is stretchy and tough. Combined with dry ice to embrittle it, the preformed film is passed through a grinder to produce a powder.

The powder is then suspended in water and applied to the skin as a watery suspension and covered with an occlusive dressing or a piece of moisture impermeable tape. A good block is established in 1½ to 2 hours.

Application of Betadine® pre-applied to the skin or used in the fluid to suspend the particles enhances the speed of onset.

TOPICAL APPLICATION OF PARTICLES EXAMPLE II

A powder is made of polyethylene oxide 33%, polyvinyl chloride 33% and lidocaine base 33%, by weight. A film of this mixture is formed in an oven at 300° F. and then ground with dry ice to produce a fine white powder. The powder is suspended in water and placed on the skin beneath an occlusive dressing. Anesthesia is established in about 1½ to 2 hours. This powder has the advantage that the polyethylene oxide component is water soluble and sticky, so that it causes the suspension to stick better to the skin than does the powder of Example I. So long as it is kept covered and remains moist, anesthesia is prolonged. In this case the PEO acts as an adherent carrier for the lidocaine base, polyvinyl chloride particles.

TOPICAL APPLICATION OF PARTICLES EXAMPLE III

The cream of Example II was employed, except the water was replaced with Betadine® scrub solution. The surgical scrub contains surfactants which speed the onset of block when this material is applied to the skin and covered with an occlusive dressing. Onset time for anesthesia was reduced from the time of Example II to about one hour.

TOPICAL APPLICATION OF PARTICLES EXAMPLE IV

An ointment was created using pulverized 50%—50% lidocaine base polyvinyl chloride film ground into a fine powder and suspended in Betadine surgical scrub. Onset of anesthesia was observed within 1 hour to 1½ hours.

Endotracheal Tubes

Another area of interest that involves lidocaine-polyvinyl chloride plastics concerns endotracheal tubes. Several research centers have recently studied transmission of lidocaine across conventional endotracheal tube cuffs. Endotracheal tubes and cuffs formed by or coated with anesthetic plastic systems according to the present invention achieve superior results from the points of view of control and duration of anesthesia and ease of use.

Delivery of Other Drugs

Most of the specific examples just given have involved the base form of local anesthetic drugs of amide or ester type in PVC, methyl methacrylate, acrylic adhesives, CPE, and EP carriers. Many other drugs with a benzene ring are relatively highly soluble or can be incorporated in PVC and other hydrophobic plastics. Similarly to the base form of local anesthetics, these drugs are slowly released to the surface of the polymer. This provides an improved mechanism for formulating time-released medications for absorption e.g. from the gastro intestinal tract or by transdermal modalities as by transdermal patch, ear or nasal plugs or foam vaginal or rectal suppositories, etc. The plugs and suppositories in some instances comprise drug incorporated in plastic foam, as mentioned above, and in other instances comprise non-drug carrying compressible or deformable members that have an exterior, drug-containing plastic film, sheet or coating according to the invention as an outer covering.

The following examples of use illustrate broad further teachings of the invention in various fields of medicine and personal care.

ALLERGISTS

Prior to applying a pattern of allergens by needle to the skin, a topically anesthetizing, pressure-sensitive adhesive covering, according to the invention, is applied to the area. This preparatory step avoids pain of the needle. It may be applied at home before visiting the allergist. When used after administration of the allergens, it can reduce itching or pain.

In various instances the covering is a film, sheet or foam of anesthetizing hydrophobic plastic, which itself, or in conjunction with a pressure sensitive adhesive layer, contains a concentration of the anesthetic in solid solution or otherwise incorporated in the plastic. It produces prolonged dosage. See also: CONSUMER-NON PRESCRIPTION; DERMATOLOGY, below.

ANESTHESIOLOGY

A topically anesthetizing endotracheal tube and cuff enable the patient to tolerate the tube without choking or bucking while use of muscle relaxants to enable tolerance of the tube may be reduced or avoided. This leads to quicker recovery of body functions following a surgical procedure. The tube enables lower levels of general anesthesia to be maintained which can reduce anesthesia-related complications. Patient head movements associated with coughing or bucking, that can disrupt delicate operations such as eye or brain surgery, can be avoided.

Patient tolerance of the tube, produced by the long-acting local-anesthetizing effect, enables more intensive administration of breathing support in recovery and intensive care units by use of ventilator machines.

BALLOONS

See TUBES and CATHETERS; FILMS, SHEETS and FOAMS.

BURN DRESSINGS, BANDAGES AND COMPRESSES

Light weight, highly flexible anesthetizing plastic film, sheet, or foam coverings, bandages or applied coatings or creams according to the invention provide long-term comfort to burns, abrasions and incision sites. Conformability of the flexible coverings to large areas of the body enables intimate application and assures long-term integrity of the product. Dosage can be regulated by prescription of the concentration of anesthetic in the plastic due to the wide range of discovered solubility, and the ability to combine the drug with a similar non-therapeutic ingredient. The concentrations of drug in the product are unmistakably identified by color, such as red, yellow and green, in descending order of concentration of the anesthetic.

The films and foams may be applied without strong adhesives and may be painlessly removed.

Films or foams can be formed by application of emulsions that form the desired anesthetizing plastic covering. These can be removed by washing when water or alcohol-soluble additives are employed.

Absorbent compresses are combined with an anesthetizing constituent. The constituent, as e.g. an array of screen-printed vinyl anesthetic spots or lines on a compress or bandage, or anesthetizing threads or fiber reservoirs, may be employed to controllably release topical anesthetic. Hydrophobic drug carrying fibers, deposits or other constituents are advantageously combined with absorptive threads or fibers to form a dual-purpose compress or bandage.

CARDIOLOGY

See ORAL MEDICATION-TIME RELEASE; TRANSDERMAL PATCHES; INSTRUMENTS AND DEVICES; TUBES AND CATHETERS.

CONSUMER NON-PRESCRIPTION PRODUCTS

A plastic strip bandage can apply its anesthetic at the absorptive compress or through the adhesive, as suggested at BURN DRESSINGS, BANDAGES AND COMPRESSES.

Thus attractive personal care products include: a spot-sized plastic strip, for sites of needle sticks as for taking blood or freezing of tissue; spot adhesive anesthetizers for insect bites; wide area anesthetizing plastic covering for skin exposed to poison ivy or poison oak or other itching conditions; a similar covering for burns; a scratch covering for the child, athlete, or adult; a painless bandage for use by infants and people with sensitive skin.

Other objects placed in a sensitive region inside or outside the body may be provided with an anesthetizing covering. Thus, a hot water bottle or an ice pack formed of PVC or having a PVC coating can administer topical anesthetic to a bruised or abraded area in conjunction with thermal therapy. Likewise anesthetizing foam cushions are achievable.

DENTISTRY

Rapid onset of topical anesthetic from foam and sheet via mucosal tissue of the mouth and gums can prepare the dental patient for a painful procedure or allay topical pain for extended periods following the procedure. An example is gum surgery. The controlled release properties due to selection of the plastic and concentration of the anesthetic produces sufficiently slow diffusion from the hydrophobic plastic to ensure that dosage is properly controlled and blood levels of lidocaine do not become excessive.

DERMATOLOGY

Anesthetic is released from films, sheets, foams, compresses, coatings and creams over selectable durations for patients with skin and neurological disorders. Patients with shingles or herpes infections or post herpes neuralgia and patients with hyper-sensitive and painful or itching skin conditions can thus be treated.

Patients can be prepared for minor skin surgery, dermabrasion, laser treatment, electrolysis or waxing by pre-application to the site to be treated. Home application of an anesthetizing covering preceding the visit to the surgeon can reduce stay in the hospital or doctor's office. Likewise, customers desiring to have tatoos applied or removed may pre-apply an anesthetizing covering to avoid pain.

FILMS, SHEETS AND FOAMS

A thin film substrate of polyvinyl chloride that is highly flexible due to the presence of a large concentration (e.g. 50%) lidocaine base, can induce topical anesthesia to mucosal tissue very quickly and to the outer skin when in place an hour or so. More rapid onset of anesthesia of the skin can be achieved by use of benign penetration agents that are included in or applied to the anesthetizing film, sheet or foam.

A film, sheet or foam containing a selected mixture of anesthetic bases, itself, has a pressure sensitive adhesive character that can enhance transfer of the drug. Supplemental adhesive such as a thin layer of acrylic adhesive can be employed for added adhesion, with the layer serving as an intermediate transfer layer.

A highly flexible non-reservoir plastic film of less than 0.001 inch thickness such as polyethylene can support a thin, effective coating of reservoir polymer for short term use measured in hours or days.

Use of a water soluble film-forming polymer as a carrier of hydrophobic reservoir resin particles in which the drug is in solid solution provides a film with a water-activated adhesive surface, which, after use, can readily be washed away.

Depending upon the thickness of the film, sheet or foam, an anesthetic effect lasting for days, weeks, or longer can be achieved. To extend the period of effectiveness, it is only necessary to increase the thickness of the reservoir layer and/or the concentration of anesthetic base in solution in the polymer, or to control other parameters of the product such as choice of the drug, the plastic resin, and the character of any metering layer.

Anesthetizing plastic films or sheets may be "lay-flat", formed by casting or extrusion through a flat die. The blown film process as used in producing packaging film may be employed, in which the anesthetic base is provided in the compounded resin that is fed to the extruder that forms a hollow tube which is then expanded by a captured bubble of air. Application of a layer of the polymer-drug combination to various preformed films, sheets or other structures is also advantageous.

In other cases, the film is formed, as by free-form blowing of a tubular parison or blowing the parison in a mold, into a desired object, for instance into the form of an inflatable balloon to occlude a body passage, as the inflatable cuff of an endotracheal tube, or the balloon of a Foley Catheter, or as a flexible obturator or probe.

In still other cases, the film is formed in situ as a coating on an object, as from solutions containing the resin and drug, from which a process solvent or carrier is evaporated.

Plastisols are likewise molded or cast to form films, sheets, foams, molded objects and coatings, and then are heated to congeal the resin as a permanent flexible structure or coating.

The density of foams that are formed depend, in the conventional way, upon the amount of blowing agent employed within the plastic-drug composition. An ear plug of plastic can administer drug via tissue in the ear, or a suppository can administer drug via rectal tissue. These may be of foam according to the invention or covered by a film or coating according to the invention.

GASTROENTEROLOGY

For naso-gastric and enteral feeding tubes, see TUBES AND CATHETERS.

INSTRUMENTS DEVICES, and IMPLANTS

Endoscopes, ultra-sound catheter probes and other probes are provided with permanent anesthetizing plastic coverings or thin disposable, anesthetizing sheaths for anesthetizing mucosal or other tissue.

Implants, cushions and other devices that contact sensitive regions can likewise have permanent anesthetizing coverings or be encased in disposable sheaths.

Consumer products include ice packs, hot water bottles and cushions. These likewise have permanent, anesthetizing covers or thin, disposable anesthetizing sheaths.

Implanted anesthetizing strips, fibers or rods or injection of body-tolerable masses of polymer reservoir material carrying the anesthetic can be introduced to painful sites such as to the site of cancer of the pancreas and exposed nerves in the posterior gutter along the spine.

NEUROLOGY

See: DERMATOLOGY; INSTRUMENTS, DEVICES and IMPLANTS; STRIPS, SUTURES, RODS, THREADS, FIBERS and NON-WOVENS.

ORAL MEDICATION-TIME RELEASE

Tiny solid polymer particles that serve as reservoirs are ingested in powder or tablet form, release the drug in a controlled manner as the particles pass through the gastrointestinal tract and are excreted. In this manner drugs such as lidocaine or propathenone, administered systemically for anti-seizure or antiarrhythmic treatment, or for migraine headache, or drugs of similar structural properties, can be administered in a time-released manner in the gastric system. The drug is absorbed through the stomach and intestinal linings to progressively enter the blood stream.

ORTHOPEDICS and PROSTHETICS

Plastic cushioning for prosthetics, such as foam coverings for artificial limbs, provide anesthetizing stump contact surfaces that alleviate itching and discomfort for an extended time. The topical anesthetic contained in the polymer, in concentrations as high as 50% by weight, is released to the skin for extended periods. This system is particularly applicable to the new stump in its first fitting of a prosthetic. The inclusion of anesthetic in plastic cartilage replacements or in methacrylate bone cement for joint replacement is also feasible.

SURGERY

Shortened hospital stay, lower hospitalization cost, more rapid rehabilitation and reduction of persistent sensitivity following healing are all made possible by the novel products that have been described. Topically anesthetizing drains, temporary anesthetizing implants and wound closings can significantly reduce pain of many surgeries. Examples are chest surgery, abdominal surgery and treatment of cancers.

See the Surgical scenario that was presented above, and: ANESTHESIOLOGY; BURN DRESSINGS, BANDAGES AND COMPRESSES; INSTRUMENTS, DEVICES AND IMPLANTS; ORTHOPEDICS AND PROSTHETICS; STRIPS, SUTURES, RODS, THREADS, FIBERS AND NON-WOVENS; AND TUBES and CATHETERS.

PODIATRY

Plasters and pads that produce prolonged relief from pain and discomfort of the feet have the construction of products described under CONSUMER NON-PRESCRIPTION; DERMATOLOGY.

The products are most effective upon areas of thin skin.

STRIPS, SUTURES, RODS, THREADS, FIBERS AND NON-WOVENS

Strips and sutures having an anesthetizing plastic exterior, formed of the reservoir polymer in which the anesthetic base is in solid solution, provide a local anesthetizing effect that decreases post-operative discomfort at the surgical site.

Conventional suture material, e.g. silk, polyester, glass or cotton suture materials have a plastisol coating applied, made of the reservoir polymer, with the drug in solid solution or otherwise incorporated. During manufacture, the plastisol is heated to congeal the polymer into a tenacious, anesthetizing suture covering.

In other cases, the sutures are monofilaments or composites that are themselves constituted of the reservoir polymer in which the drug is in solid solution or otherwise incorporated. Reinforcing fibers within the polymer render the suture inextensible.

Monofilaments may be extruded and drawn from a die, or a series of filaments may be twisted or otherwise formed into an extensible or nonextensible thread or yarn.

The fine constituent fibers of a non-woven fabric can likewise be formed by drawing of melted-anesthetic plastic from spinnerrettes followed by treatment to form the fibers into fabrics. Air laying, bonding or hydroentanglement are suitable non-woven-forming techniques for the anesthetic plastics, depending upon the choice of resin. The fibers in staple form may likewise be employed in a non-woven construction. An adhesive material used to bond fibers to form a non-woven fabric may also constitute a polymeric reservoir for the base form drug.

Rods of reservoir polymer may be formed by extrusion techniques, with the drug incorporated in the feed compound to the extruder, or may be formed by extrusion of a plastisol of reservoir resin and drug, followed by curing, or by casting. The rods may be highly flexible, for use within the body at places of flexing. They may have elastomeric properties, to permit stretching to conform to body movements. In other cases the rods may be nonextensible, e.g. fiber reinforced, to facilitate removal from the body by application of tension.

TRANSDERMAL PATCHES

Rugged transdermal skin patches employ large concentrations of selected drugs in solid solution in durable polymers. An example is lidocaine in base form in solid solution 50% by weight in polyvinyl chloride strips, or lidocaine, 30% by weight in acrylic adhesive compositions.

A combination of a plastic strip reservoir, in which a high concentration of drug is in solid solution or otherwise incorporated, and an adhesive layer, also containing the drug, provides an effective system for attachment of the patch to a transfer region on the body, as behind the ear. In this example, the adhesive mass serves as the transfer layer, and is continuously resupplied by the solid plastic strip reservoir to achieve long term transdermal dosage.

In transdermal systems according to the techniques disclosed there is no need to be concerned about the protection of liquids or delicate gels. Benefits include simpler packaging and storage, avoidance of need for precautions in user handling, and lowered cost.

One use for such a skin patch is for prolonged administration of propafenone or lidocaine for antiarrythmia or antiseizure medication or of lidocaine systemically for migraine headache. For the migraine application, the patch serves as a substitute for nasal spray administration of lidocaine that risks uncomfortable sensations if the sprayed lidocaine enters the throat from the nose.

TUBES AND CATHETERS

The exteriors of tubes and catheters are provided with an anesthetizing surface either in the form of a solvent-based coating or plastisol coating, or by having the structure of the tube or device fabricated of the polymer-anesthetic material, as by extruding or by casting of a plastisol.

Examples are, catheters, such as Foley catheters, urethral and ureteral catheters, endotracheal tubes, feeding tubes including naso-gastric and enteral feeding tubes, drains including Penrose drains, drainage stents, shunts, sheaths and reinforcing stents. The tubular devices themselves, or disposable sheaths for these devices, may be anesthetizing. Permanent lubricious coatings are provided on the exterior of catheters and other tubes, or lubricious coatings are applied at the time of use, that contain polymer-topical anesthetic constituents for numbing the contacted mucosal tissue during insertion and manipulation of the catheter.

UROLOGY

The tubes and balloons of Foley catheters are provided with a covering, or the balloon wall is formed solidly from the anesthetic plastic system. Likewise, urethral and ureteral catheters, stents and shunts can be formed or coated. All can have a unique anesthetizing effect that promotes comfortable tolerance. The tubes and catheters may be provided with an anesthetizing lubricious coating.

For more rapid onset, an initial water-soluble form of the anesthetic, such as lidocaine hydrochloride may be presented at the outer surface of any of these devices for achieving rapid anesthesia during initial introduction.

VETERINARY

The veterinary applications correspond to the medical applications that have been described. Pets and other animals will be less likely to disturb wound dressings, bandages, casts and transdermal patches that incorporate anesthetizing plastic.

What is claimed is:

1. A transdermal drug delivery system including a drug delivery polymer in which a drug in the polymer has an aromatic ring, the drug incorporating at least one free amide or amine hydrogen in its structure, the polymer being hydrophobic and thermoplastic, the drug being soluble in the polymer in a concentration of at least 20% by weight, and the drug being in solution in the polymer in an effective concentration in excess of 20% by weight, the polymer being in the form of a layer adhered to a carrier sheet, the layer comprising pressure-sensitive adhesive adapted to adhere to skin.

2. A transdermal drug delivery system including a drug delivery polymer in which a drug in the polymer has an aromatic ring, the drug incorporating at least one free amide or amine hydrogen in its structure, the polymer being hydrophobic and thermoplastic, the polymer being in the form of a non-adhesive layer of polymeric resin in which the drug is in substantial solution, and an adjoining adhesive band arranged to hold the non-adhesive layer against the skin, the drug being soluble in the polymer in a concentration of at least 20% by weight, and the drug being in solution in the polymer in an effective concentration in excess of 20% by weight.

3. The transdermal drug delivery system of claim 1 or 2 in which the drug is a topical anesthetic drug in base form.

4. The transdermal drug delivery system of claim 1 or 2 wherein the drug has the structure

where:

Bz is a substituted or unsubstituted benzene ring;

Z is an ester or amide linkage;

and each $R^1$ and $R^2$, individually, is Hydrogen or an alkyl group, or together form a 5 or a 6 member ring with the Nitrogen, and n is an integer.

5. The transdermal drug delivery system of claim 1 or 2 in the form of a transdermal patch in which the drug comprises a topical anesthetic compound in base form, which is more soluble in the polymer than in water, the amount of the anesthetic compound incorporated in the polymer rendering the composition suitable as a topical anesthetic agent.

6. The transdermal patch of claim 5 in which the anesthetic compound is selected from the group consisting procaine, mepivacaine, bupivicane, lidocaine, chloroprocaine, tetracaine, etidocaine, prilocaine, etidocaine, replivicaine, diphenhydramine and benzocaine.

7. The transdermal patch of claim 5 in which the polymer and anesthetic compound are present as a transparent layer.

8. The transdermal drug delivery system of claim 1 in which the drug is an anesthetic base selected from the group consisting of procaine, mepivacaine, bupivicane, lidocaine, chloroprocaine, tetracaine, etidocaine, prilocaine, etidocaine, replivicaine, diphenhydramine and benzocaine.

9. The composition of claim 1 or 2 wherein the drug comprises propafenone.

10. The transdermal drug delivery system of claim 1 in which the layer comprising pressure sensitive adhesive has solids in which the drug is substantially soluble, a non-adhesive polymeric resin distributed uniformly in non-particulate manner through the adhesive, and said drug.

11. The transdermal drug delivery system of claims 1, 10 or 2 in which the layer is sufficiently thin that there is no more than about 30 mg per inch square of drug present in the layer.

12. The transdermal drug delivery system of claim 2 in which the polymeric resin and the drug comprise a congealed plastisol.

13. The transdermal drug delivery system of claims 1, 10 or 2 in which the layer is transparent.

14. The transdermal drug delivery system of claim 13 in which the layer is disposed on a transparent carrier sheet.

15. The transdermal drug delivery system of claims 1, 10, or 2 in which the drug is active upon nerves or an aspect of the nervous system.

16. The transdermal drug delivery system of claims 1, 10, or 2 in which the drug is an anesthetic, topical anesthetic, analgesic, a narcotic or opiate, or a stimulant of the nervous system.

17. The transdermal drug delivery system of claims 1, 10, or 2 in which the drug has local anesthetic properties, or is an antiarrhythmic or antiseizure drug, an adrenergic blocking drug, a sympathomimetic drug, an analgesic or antipyretic drug or a drug that stimulates the nervous system.

18. The transdermal drug delivery system of claims 1, 10 or 2 in which the drug comprises at least two drugs, one of which is soluble in the other, a solution of at least two drugs in the relative quantities present in the layer having a melting temperature below room temperature, and lower than the melting temperature of either drug alone.

19. The transdermal drug delivery system of claim 18 in which one of the drugs is an ester and one of the drugs is an amide.

20. The transdermal drug delivery system of claim 18 in which one of the drugs is tetracaine and one of the drugs is lidocaine.

21. The transdermal drug delivery system of claim 1 or 10 in which the adhesive is an acrylic adhesive of methacrylate resin.

22. The transdermal drug delivery system of claims 1, 10, or 2 in which the polymer or polymeric resin comprises PVC polymer.

23. The transdermal drug delivery system of claims 1, 10, or 2 in which the polymer or polymeric resin is selected from the group consisting polymers and copolymers of polyvinylchloride, other polymerized vinyl halides, chlorinated polyethylene, other halogenated polyolefins, ethylene propylene, cellulose resins such as cellulose nitrate, ethyl cellulose, and cellulose acetate, polystyrene, polyvinyl butyryl, acrylic resins, alkyl alkylacrylates, alkyl acrylates, acrylonitrile rubbers and chlorinated rubbers, polyesters, polyamides and polyformaldehyde.

24. The transdermal drug delivery system of claims 1, 10, or 2 in which the drug is selected from the group consisting of procaine, mepivacaine, bupivicane, lidocaine, chloroprocaine, cocaine, tetracaine, etidoncaine, prilocaine, etidocaine, replivicaine, diphenhydramine, and benzocaine.

25. The transdermal drug delivery system of claims 1, 10, or 2 in which the drug is fentanyl.

26. The transdermal drug delivery system of claim 2 in combination with a cushion arranged to press the drug-containing layer against the skin.

27. A transdermal drug delivery system including a drug delivery polymer in which a drug in the polymer has an aromatic ring, the drug incorporating at least one free amide or amine hydrogen in its structure, the polymer being hydrophobic and thermoplastic, the drug being soluble in the polymer in a concentration of at least 20% by weight, and the drug being in solution in the polymer in an effective concentration in excess of 20% by weight, the polymer being in the form of a pressure sensitive adhesive comprising medical grade pressure sensitive acrylic adhesive and polyvinyl chloride, the drug being in the form of one or more topical anesthetics in base form.

28. A transdermal drug delivery system including a drug delivery polymer in which a drug in the polymer has an aromatic ring, the drug incorporating at least one free amide or amine hydrogen in its structure, and comprising one or more topical anesthetics in base form, the polymer being hydrophobic and thermoplastic, the drug being soluble in the polymer in a concentration of at least 20% by weight, and the drug being in solution in the polymer in an effective concentration in excess of 20% by weight, the polymer being polyvinyl chloride and the drug delivery system being in the form of a plastisol comprising said one or more topical anesthetics in base form and said polyvinyl chloride.

29. The transdermal drug delivery component of claim 27 in which the polyvinylchoride is distributed in the adhesive uniformly in a non-particulate manner.

30. The transdermal drug delivery system of claim 27, 29, or 28 in combination with a volatile alcohol as a paintable, coatable or sprayable composition onto the skin.

31. The transdermal drug delivery system of claim 27, 29, or 28 containing at least two miscible anesthetic bases, as drugs, in which the ratio of the weight of the two drugs, combined, to the weight of the combined adhesive solids and polyvinylchloride, or the polyvinylchloride when it appears alone, is greater than 50%.

32. A transdermal drug delivery system including a drug delivery polymer in which a drug in the polymer has an aromatic ring, the drug incorporating at least one free amide or amine hydrogen in its structure, and comprising one or more topical anesthetics, the polymer being hydrophobic and thermoplastic, the drug being soluble in the polymer in a concentration of at least 20% by weight, and the drug being in solution in the polymer in an effective concentration in excess of 20% by weight, the drug delivery system being in the form of a congealed plastisol layer comprising said one or more topical anesthetics in base form and said polyvinyl chloride.

* * * * *